United States Patent
Shieh et al.

(10) Patent No.: US 7,920,914 B2
(45) Date of Patent: Apr. 5, 2011

(54) METHOD FOR MONITORING THE DEPTH OF ANESTHESIA

(75) Inventors: Jiann-Shing Shieh, Taipei (TW); Bo-Cun Chen, Su-ao Township, Yilan County (TW); Shou-Zen Fan, Taipei (TW)

(73) Assignee: Yuan Ze University, Taoyuan County (TW)

( * ) Notice: Subject to any disclaimer, the term of this patent is extended or adjusted under 35 U.S.C. 154(b) by 95 days.

(21) Appl. No.: 12/372,666

(22) Filed: Feb. 17, 2009

(65) Prior Publication Data

US 2009/0177108 A1   Jul. 9, 2009

Related U.S. Application Data

(63) Continuation-in-part of application No. 11/734,478, filed on Apr. 12, 2007, now abandoned.

(51) Int. Cl.
    *A61B 5/04* (2006.01)
(52) U.S. Cl. ....................................................... 600/544
(58) Field of Classification Search .................. 600/544, 600/545
    See application file for complete search history.

(56) References Cited

U.S. PATENT DOCUMENTS

| | | | |
|---|---|---|---|
| 6,631,291 B2 * | 10/2003 | Viertio-Oja et al. | 600/544 |
| 6,731,975 B1 * | 5/2004 | Viertio-Oja et al. | 600/544 |
| 6,801,803 B2 * | 10/2004 | Viertio-Oja | 600/544 |
| 7,228,169 B2 * | 6/2007 | Viertio-Oja et al. | 600/544 |
| 7,231,246 B2 * | 6/2007 | Rautee et al. | 600/544 |
| 7,509,161 B2 * | 3/2009 | Viertio-Oja | 600/544 |
| 7,549,959 B2 * | 6/2009 | Takala et al. | 600/300 |
| 7,630,758 B2 * | 12/2009 | Lapinlampi et al. | 600/544 |
| RE41,291 E * | 4/2010 | Viertio-Oja et al. | 600/544 |
| 7,725,174 B2 * | 5/2010 | Kern et al. | 600/544 |

OTHER PUBLICATIONS

Tetsuya Miyashita et al., Spectral analyses of electroencephalography and heart rate variability during sleep in normal subjects, Journal, Oct. 31, 2002, pp. 114-120, Elsevier Science B.V.

Jorgen Bruhn et al., Approximate Entropy as an Electroencephalographic Measure of Anesthestic Drug Effect during Desflurane Anesthesia, Journal, Mar. 2000, vol. 92 No. 3, pp. 715-726, American Society of Anesthesiologist, Inc., Lippincott Williams & Wilkins, Inc.

(Continued)

*Primary Examiner* — John P Lacyk
*Assistant Examiner* — Navin Natnithithadha
(74) *Attorney, Agent, or Firm* — WPAT, P.C.; Anthony King

(57) ABSTRACT

A method for monitoring the depth of anesthesia is provided for detecting the conscious state of one being anesthetized in the recovery phase or induction phase of anesthesia course in order to facilitate an anesthesiologist to predict exactly the dosage of an anesthetic required. At first, an original electroencephalogram (EEG) is taken from one being tested. Then, the original electroencephalogram is analyzed by approximate entropy to obtain its approximate entropy value. Next, the approximate entropy value is multiplied by 1000/17, and the corrected value is assumed as the predicted value of depth of anesthesia. The predicted value of depth of anesthesia represents degree of the conscious state or the depth of anesthesia for the one being tested. The higher the predicted depth of anesthesia value, the more conscious the one being tested is, i.e., in a shallower depth of anesthesia. On the other hand, the lower the predicted depth of anesthesia value, the less conscious the one being tested is, i.e., in a deeper depth of anesthesia.

8 Claims, 16 Drawing Sheets

OTHER PUBLICATIONS

Vikram K Yeragani et al., Approximate entropy of symptoms of mood: an effective technique to quantify regularity of mood, Journal, 2003, pp. 279-286, Blackwell Munksgaard.

L Diambra et al., Epileptic activity recognition in EEG recording, Journal, 1999, pp. 495-505, Elsevier Science B.V.

Stephanie A Caswell Schuchers et al., Use of Approximate Entropy Measurements to Classify Ventricular Tachycardia and Fibrillation, Journal, 1998, vol. 31, pp. 101-105, Churchill Livingstone.

Valerie Billard et al., A Comparison of Spectral Edge, Delta Power, and Bispectral Index as EEG Measures of Alfentanil, Propofol, and Midazolam Drug Effect, Journal, Jan. 1997, pp. 45-58, vol. 61 No. 1, Clinical Pharmacology & Therapeutics.

Walter S. Pritchard et al., Measuring "Chaos" in the Brain: A Tutorial Review of EEG Dimension Estimation, Journal, 1995, pp. 353-397, vol. 27, Academic Press, Inc.

Jurgen Fell et al., Discrimination of Sleep Stages: A Comparison Between Spectral and Nonlinear EEG Measures, Journal, 1996, pp. 401-410, vol. 98, Electroencephalography and Clinical Neurophysiology, Elsevier.

Peter Grassberger et al., Estimation of the Kolgmogorov Entropy from a Chaotic Signal, Journal, Oct. 1983, pp. 2591-2593, vol. 28 No. 4, The American Physical Society.

Helmut Schwilden et al., Quantitative EEG Analysis During Anaesthesia with Isoflurane in Nitrous Oxide at 1.3 and 1.5 MAC, Journal, 1987, pp. 738-745, vol. 59, British Journal of Anaesthesia.

Takasumi Katoh et al., Electroencephalographic Derivatives as a Tool for Predicting the Depths of Sedation and Anaesthesia Induced by Sevoflorane, Journal, 1998, pp. 642-650, vol. 88 No. 3, American Society of Anesthesiologist, Inc., Lippincott-Raven Publishers.

Thomas Elbert et al., Chaos and Physiology: Deterministic Chaos in Excitable Cell Assemblies, Journal, Jan. 1994, pp. 1-47, vol. 74 No. 1, The American Physiological Society.

J.-P. Eckmann et al., Ergodic Theory of Chaos and Strange Attractors, Journal, Jul. 1985, pp. 617-656, vol. 57 No. 3, The American Physical Society.

Bo-Cun Chen et al., The Approximate Entropy and the Complexity theories establish the depth of anaesthesia system, Thesis, Jun. 2006, Yuan Ze University, Chungli Taiwan.

Pritchard, et al, Measuring Chaos in the Brain: A tutorial review of nonlinear dynamical analysis, Journal, 1992, Brain J. Neurosci. vol. 67, pp. 31-80.

* cited by examiner

METHOD FOR MONITORING THE DEPTH OF ANESTHESIA

CROSS-REFERENCE TO RELATED APPLICATIONS

This application claims priority to, and is a Continuation-in-part of, U.S. patent application Ser. No. 11/734,478, filed on Apr. 12, 2007, now pending, which is hereby incorporated by reference in its entirety.

Although incorporated by reference in its entirety, no arguments or disclaimers made in the related application apply to this application. Any disclaimer that may have and occurred or might occur during the prosecution of the above-referenced application is hereby expressly rescinded.

BACKGROUND OF THE INVENTION

1. Field of the Invention

The invention relates to a method for monitoring the depth of anesthesia, and in particular, a method for monitoring the depth of anesthesia based on the theory of approximate entropy.

2. Description of the Prior Art

Anesthesia is an indispensable part of surgery. In the course of operation, either over or under dosage of anesthetics will cause adverse effects on the patient. As a traditional anesthesia method, an anesthesiologist monitors depth of anesthesia in a patient under anesthesia based on observations on the underlying change of physiological symptoms such as breathing rates, the blood pressure, the heart beat, eye signs and the like as well as the patient's physical response to stimulation caused by the operation procedure. However, in the process of anesthesia, a muscle relaxant might be used as an auxiliary drug to have better muscle relaxant effect on the patient during the surgical operation. A muscle relaxant itself exhibits neither an analgesic action nor an anesthesia action. Furthermore, since patients under such situations cannot breathe by themselves and are inactive, a false perceived depth of anesthesia may be consequently produced. Thereby, the anesthesiologist might lose an important objective estimation criterion, and hence could not readily monitor or detect the true anesthesia state of a patient.

In recent years, owing to the research and analysis on electroencephalogram (EEG), a dramatic progression on the determining of depth of anesthesia has occurred. The principle of brain wave measurement relies on the vertical arrangement of pyramidal neurons distribution in the human cerebral cortex. The dendrite or cell body (or soma) in these pyramidal neurons can generate local potential variation during activity, i.e., the so-called physiological potential. These potential variations can be recorded by attaching electrodes to the patient. The physiological potential of the brain wave is generally very weak, approximately at 5-30 μV, and resides in the type of alternative signal of 0.5-60 Hz. Based on the difference of frequency, EEG can be classified into 4 types: Delta wave (0.5~4 Hz), Theta wave (4~8 Hz), Alpha wave (8~13 Hz), and Beta wave (13~32 Hz).

Alpha wave appears as the main brain wave when a patient is at a static state, during rest, and eyes closed, and it disappears as eyes open. Beta wave occurs often in the period of strong mental activity. Theta and delta waves are associated with sleep and brain pathology. Clinically, brain wave characteristics can be utilized in the diagnosis or understanding of the electrical discharge of the cranial nerve cell. For example, in case of epilepsy, brain tumor, or brain injury, an abnormal discharging cranial nerve cell might evoke a synchronous electrical discharge by surrounding cranial nerve cells. Upon signal transmitting and aggregating, a distinct spike signal will occur. By virtue of the feature of a multiple point cranial nerve wave, an abnormal discharging location can be deduced. In the phase of sleep, the brain wave will exhibit some special wave forms such as k-complex and sleep spindle. In the recovery course after a brain damage or oxygen deficiency, the brain wave will present a feature of burst suppression. Based on the relatively complex feature presented in the brain wave, research can be made in terms of a frequency domain and a time domain.

In the aspect of frequency domain analysis, Schwilden and Stoeckel[1] investigated the energy distribution of the delta, theta, alpha, and beta waves in patients injected with isofurane, using fast Fourier transformation (FFT). They have found that, prior to injecting the patient with isofurane, a higher expression of the energy of beta wave occurred. However, after injecting the patient with isofurane, the energy of alpha wave became higher while the energy of beta wave decreased. Accordingly, it was suggested that the degree of consciousness of the patient could be correlated with energy of alpha and beta waves. Katoh et al.[2] analyzed the median frequency energy distribution of patients as they received sevoflurane anesthesia by using median edge frequency (MEF) and spectral edge frequency 95 (SEF95). MEF theory defines the energy distribution change below 50% of total energy as the brain wave is in the frequency domain range of 0.5-30 Hz. The SEF95 theory defines the energy distribution change below 95% of total energy as the brain wave is in the frequency domain range of 0.5-30 Hz. Katoh et al. have found that changes of SEF95 and MEF could be correlated intimately with the concentration of sevoflurane. As the concentration of sevoflurane increased, energy distributions both of SEF95 and MEF would tend to be low. On the other hand, as the concentration of sevoflurane decreased, both energy distributions would increase. However, when the electric resistivity on the skin of a patient is high, the predictability from both of SEF95 and MEF is poor. Miyashita et al.[3] studied changes of the brain wave and heart beat variation during sleeping as well as in conscious state. They analyzed brain wave in terms of SEF50, SEF90, and SEF95, and also analyzed the low frequency/high frequency (LF/HF) ratio for the heart beat variation by using FFT. The study pointed out that when people were sleeping, the energy distributions of SEF50, SEF90 and SEF95 tended to be lower than those in consciousness, and the variation of the value of SEF95 is the most significant one among them. Furthermore, the LF/HF ratio in sleep tended also to be less than the LF/HF ratio in consciousness. Billard et al.[4] analyzed the degree of anesthesia for patients who received different anesthetics such as alfentanil, propofol, and midazolam through SEF95, Delta Power, and Bispectrum Index (BIS). The study revealed that, no matter what anesthetic, either alfentanil, propofol or, midazolam, were received by a patient, BIS can distinguished equally well whether the patient is in consciousness or in anesthesia state, while SEF95 can only differentiate conscious states between patients received propofol and midazolam.

In the aspect of time domain, Elbert et al.[5] and Pritchard and Duke et al.[6] believed that a brain wave signal was not composed of a sine wave, rather the brain wave signal was a disorderly and confused, irregular signal. Therefore, they proposed the analysis of brain wave signal by means of a nonlinear method. Fell et al.[7], Grassberger and Procaccia et al.[8] as well as Eckmann and Ruelle[9] analyzed the regularity of a nonlinear signal by using different types of entropy. Till 1991, Bruhn et al.[10] proposed the application of approximate entropy (ApEn) on the nonlinear analysis of physiological signal. Furthermore, Yeragania et al.,[11] collected brain wave signals from patients under desflurane anesthesia, and analyzed the regularity within these signals by approximate entropy. They revealed that brain waves of patients displayed an irregular change before anesthesia while exhibited a regular change after anesthesia. In addition, approximate entropy is applied frequently for the differentiation of diseases. For example, Diambra et al.[12] tried to analyze EEG signals from healthy people and patients with epilepsy by approximate entropy. They have found that the value of approximate entropy from patients with epilepsy was less significantly than that of healthy people. Suchuckers[13] used approximate entropy instead of standard deviation analysis to distinguish the difference of heart beat between ventricular fibrillation and non-ventricular fibrillation, because the traditional standard deviation analysis failed to observe the regularity of a signal and also could not differentiate effectively a disease. The results indicated that patients with ventricular fibrillation and ventricular tachycardia had a value of approximate entropy significantly higher than that of normal people.

At present, to monitor and detect the depth of anesthesia, other than basing on one's experience, an anesthesiologist also monitors and detects depth of anesthesia based on some of the most commonly used methods such as Bispectrum Index (BIS) and Auditory Evoked Potential (AEP). Both of these methods measure the EEG of the anesthetized subject. BIS is based on Bispectrum and in conjunction with the anesthesia consciousness index induced from a great deal of patient data. The theory underlying BIS has not been publicly disclosed yet. On the other hand, AEP makes use of one's auditory response to measure the depth of anesthesia of a patient, since the auditory function is the sensory function that is restored first, and the lost last, in the course of anesthesia. In addition, the brain wave at middle latency is associated with anesthesia and its measuring method comprises of stimulating the one being test with a 6 Hz sound wave. Immediately after completion of each sound stimulation, the instrument takes a brain wave sample of 120 ms with a sampling frequency of 1 kHz. Thereafter, it calculates the average value of these 120 ms data. Nevertheless, since BIS and AEP equipments are expensive, they are not widely available in every operation room and in every hospital. Moreover, since its theory has not been fully disclosed, physicians cannot effectively master material information to monitor and detect depth of anesthesia, which in turn may result in anesthesia of a patient that is of too deep or too shallow. Such undesirable situation increases the risk in the operation.

Accordingly, the methods for predicting depth of anesthesia mentioned above have many disadvantages, and they are not perfect designs and need to be improved urgently.

In view of various disadvantages derived from the conventional methods for predicting depth of anesthesia mentioned above, the inventors have devoted to improve and innovate, and after intensive studying for many years, they developed finally and successfully a method for predicting depth of anesthesia, thereby accomplished the invention. All referenced patent and non-patent prior art are incorporated herein by reference in their entirety.

SUMMARY OF THE INVENTION

The invention provides a method for predicting depth of anesthesia. The method can be used for detecting the conscious state of the one being anesthetized in order to enable an anesthesiologist to predetermine the required dosage of anesthetics. The method comprises the following steps:

Step 1: attaching measuring patch on the center, ground, and right of the brow of the subject and using electroencephalography (EEG) monitor to measure electroencephalogram (EEG) from the subject being tested;

Step 2: a computer records the electroencephalography (EEG) data from electroencephalography (EEG) monitor in the recovery phase or induction phase of anesthesia course Step 3: using a computer to calculate the approximate entropy value from the recorded electroencephalogram (EEG) signal using the formula Approximat Entropy=$\Phi^m(r)-\Phi^{m+1}(r)$;

wherein $$\Phi^m(r) = (N - m + 1)^{-1} \cdot \sum_{i=1}^{N-m+1} \ln C_i^m(r);$$

$C_i^m(r)$=(number of x(j) such that d[x(i),x(j)]≦r)/(N−m+1);

x(i)=[u(i), . . . , u(i=m−1)];

x(j)=[u(j), . . . , u(j=m−1)];

u(i),u(2) . . . u(N) are time sequence data;

wherein N is the length of data cycle;

m is the number of data comparison;

r is a noise filtering coefficient;

Step 4: Using a computer to compute corrected approximate entropy value by multiplying the approximate entropy value obtained in step 2 to 1000/17;

Step 5: displaying calculated corrected approximate entropy value on a monitor as the subject's the depth of anesthesia state;

wherein, the sampling time of the electroencephalogram is 1/256 to 1/128 second/time; and the computer recorded 1024 electroencephalography (EEG) data point each time for computation.

the N. is 1024;

the m is 2; and the r is 0.2;

and wherein the predicting value of depth of anesthesia represents the degree of the conscious state or depth of anesthesia of the one being tested. As the predicting value of depth of anesthesia is higher, the conscious state of the one being tested is more conscious or the depth of anesthesia is shallower. On the other hand, as the predicting value of depth of anesthesia is lower, the conscious state of the one being tested is in more confusion or deep depth of anesthesia. The predicting value of depth of anesthesia can be divided into four grades as follows:

(1) 70-100: the one being tested is in a conscious state or slightly sedated state and is freely movable.

(2) 60-70: the one being tested is in a slight non-conscious state or gradually restoring the conscious state and the state occurred in a patient is just at the end of the operation but not regaining consciousness.

(3) 40-60: the one being tested is in a non-conscious state. A patient undergoing an operation should be controlled within this range of depth of anesthesia, which indicates the optimal dosage range.

(4) 0-40: the one being tested is in an excessively non-conscious state. If the one being tested is a patient in an operation room, this indicates the over dosage of anesthetics that makes the depth of anesthesia of the patient being into excessively deep.

These features and advantages of the present invention will be fully understood and appreciated from the following detailed description of the accompanying Drawings.

BRIEF DESCRIPTION OF THE DRAWINGS

FIG. 3-1 to 3-25 show results of the analysis for conscious states of the subject being test at various anesthesia phase using BIS Index, SEF95, MEF, and approximate entropy.

DETAILED DESCRIPTION OF THE PREFERRED EMBODIMENT

Example 1

The Collection of Clinical Data

1. The Investigated Subject

The investigated subjects of this example were patients to be subjected to an operation of nasosinusitis in National Taiwan University Hospital. Twenty-five patients were enrolled. Thirteen of them are male, and the other twelve are female. They are in an average age of 42±13 years, and the average operation time is 110±45 minutes. The patient being tested was made first into anesthesia by intravenous injecting with thiopental. Then, the anesthesia manner was changed into general gas anesthesia (general anesthesia using inhalant anesthetics), which the main inhalant anesthetics were isoflurane, sevoflurane, and desflurane.

2. Measuring Instruments and Data Collection

Figure 1:
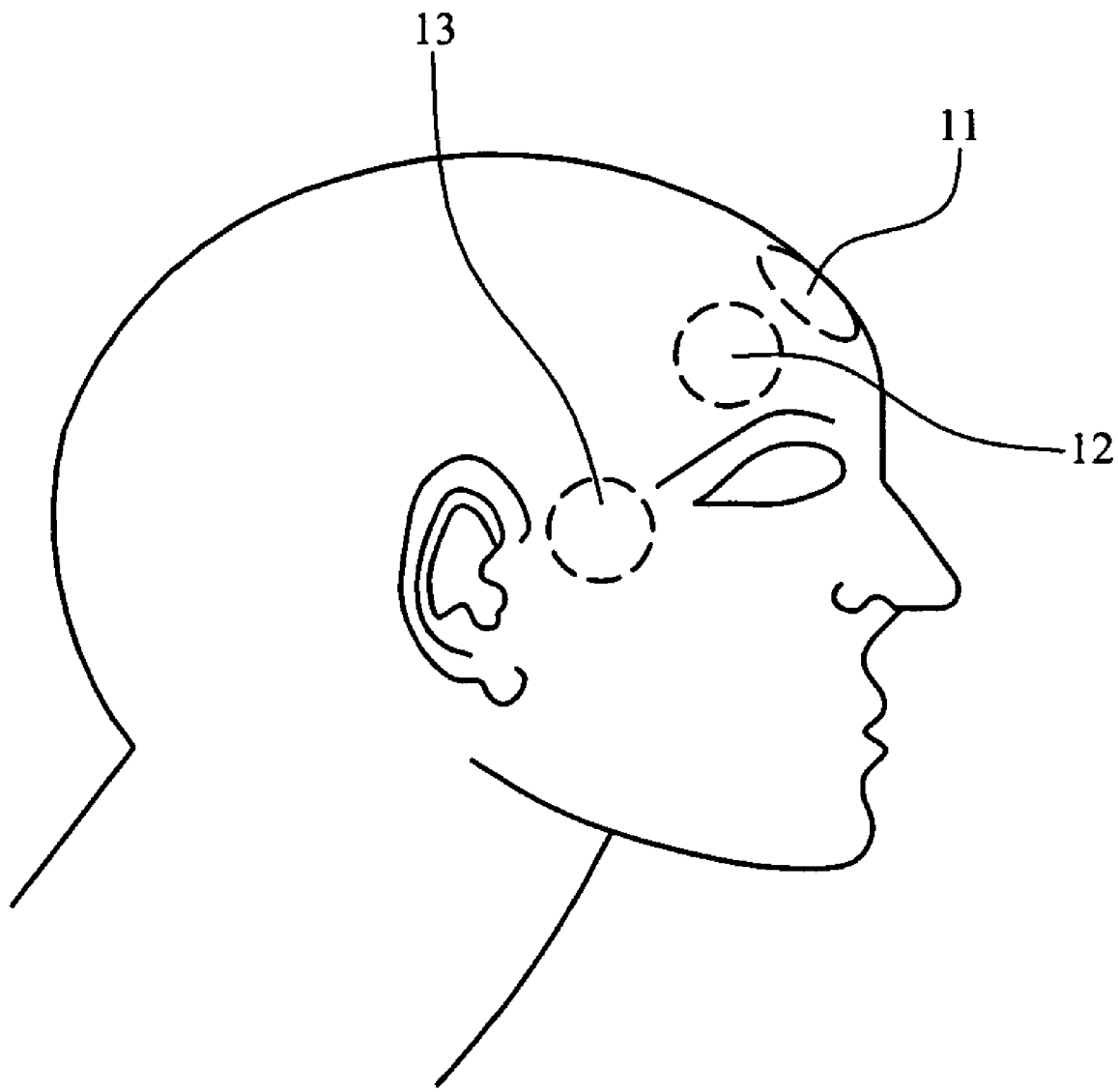
FIG. 1 shows the position where the brain wave measuring patch is attached.
Figure 2A:
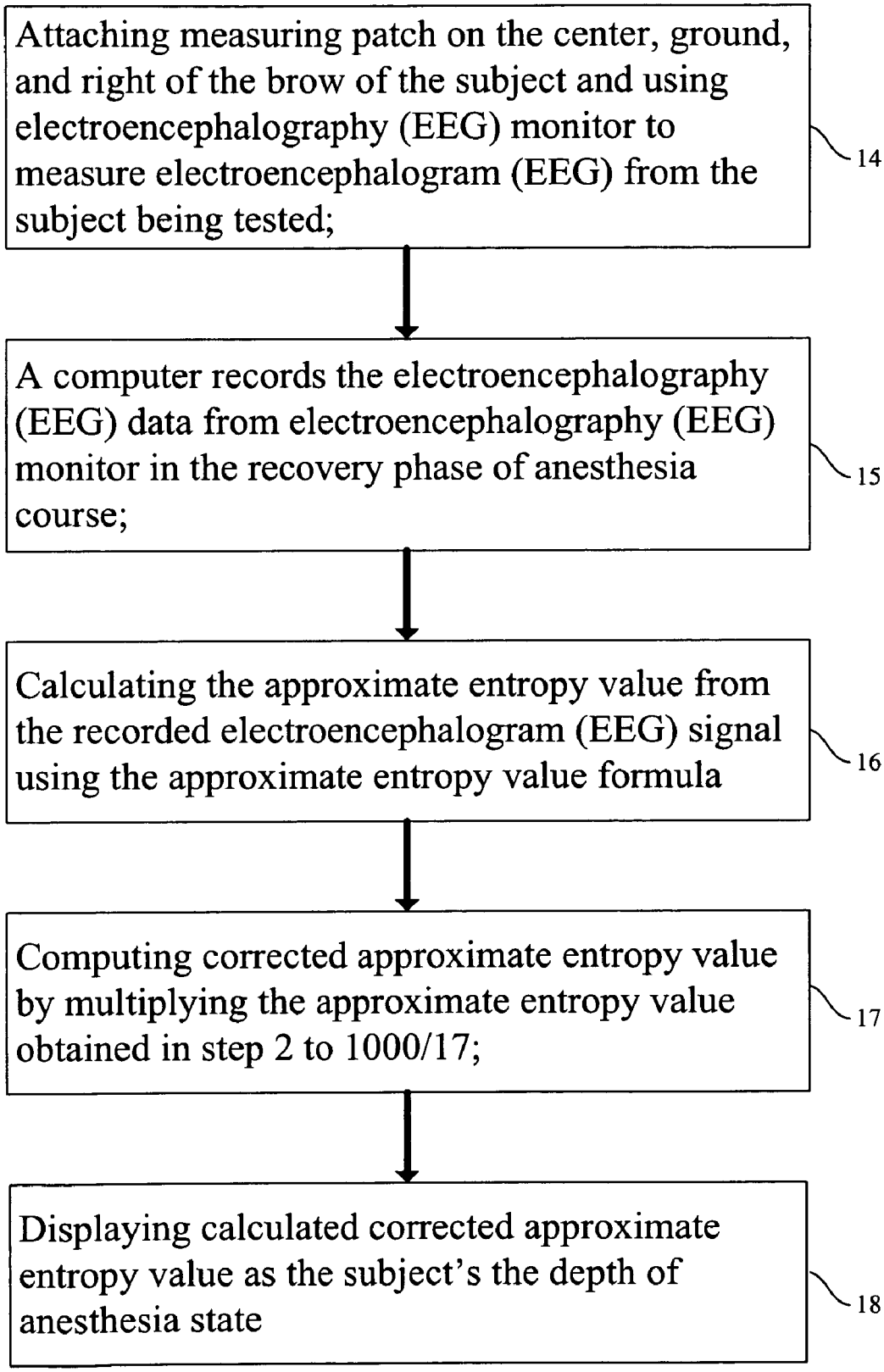
FIG. 2A is a flow chart illustrating the method for monitoring the depth of anesthesia.

Referring to FIG. 2A number 14, a method for predicting the depth of anesthesia, comprising step 1: attaching measuring patch on the center, ground, and right of the brow of the subject and using electroencephalography (EEG) monitor to measure obtaining original electroencephalogram (EEG) from one the subject being tested. In this example, the brain wave signal, BIS Index, SEF95, and MEF of the anesthetized subject was collected with a BIS Monitor (Aspect A-1050). As shown in FIG. 1, the brain wave measuring patch was attached on the center (CTR) 11, ground (GND) 12, and right (R) 13 of the brow of the subject. The sampling time for BIS Index, SEF95, and MEF data was 5 sec/time. The sampling time for EEG data was 1/128 sec/time. The brain wave monitor was connected to a computer through RS232. All of the data measured were transmitted to the computer for analysis.

BIS Index was used to indicate the degree of conscious state and the depth of anesthesia or tranquilization based on a scale of 0-100. Generally, it can be divided into four grades as follows:

(1) 70-100: the subject is in a conscious state or slightly sedation state and is freely movable. The BIS Index is usually in the range of 90-100.
(2) 60-70: the subject is in a slight non-conscious state or gradually restoring the conscious state and the state occurred in a patient is just at the end of the operation but not regaining consciousness.
(3) 40-60: the subject is in a non-conscious state. In general, a patient undergoing an operation should be controlled within this range of depth of anesthesia, which indicates the optimal dosage range.
(4) 0-40: the subject is in an excessively non-conscious state. If the subject is a patient in an operation room, this indicates the over dosage of anesthetics that makes the depth of anesthesia of the patient being into excessively deep.

In addition, values of SEF95 and MEF obtained from BIS Monitor were in the range of 0.5-30 Hz. MEF defines the energy distribution change below 50% of total energy as the brain wave is in the frequency domain range of 0.5-30 Hz. SEF95 defines the energy distribution change below 95% of total energy as the brain wave is in the frequency domain range of 0.5-30 Hz. The more conscious the subject is, the frequency value is closer to 30 Hz. On the contrary, as the subject in low consciousness, the frequency value is closer to 0.5 Hz. For comparing conveniently with other method, in this example, values of SEF95 and MEF were set in the range of 0 to 100, where 0 represented 0.5 Hz, and 100 represented 30 Hz.

Referring to FIG. 2A number 15, a method for predicting the depth of anesthesia, comprising step 2: a computer records the electroencephalography (EEG) data from electroencephalography (EEG) monitor in the induction phase or recovery phase of anesthesia course. In this example, the anesthesia course was divided into three phases, i.e. induction, maintenance, and recovery, so as to analyze the depth of anesthesia of the subject in terms of various phases.

(1) The induction phase: from 1 minute after intravenous injecting thiopental to 1 minute after inhalating the inhalant anesthetics.
(2) The maintenance phase: from 1 minute after inhalating the inhalant anesthetics to 1 minute after stopping the inhalation of the inhalant anesthetics.
(3) The recovery phase: from 1 minute after stopping the inhalation of the inhalant anesthetics till the subject regains consciousness.

Example 2

Analysis of Brain Wave Signals with Approximate Entropy

Referring to FIG. 2A number 16, a method for predicting the depth of anesthesia, comprising step 3: using a computer to calculate the approximate entropy value from the recorded electroencephalogram (EEG) signal using the formula $$\text{Approximat Entropy} = \Phi^m(r) - \Phi^{m+1}(r);$$

wherein $$\Phi^m(r) = (N-m+1)^{-1} \cdot \sum_{i=1}^{N-m+1} \ln C_i^m(r);$$

$C_i^m(r)$ = (number of $x(j)$ such that $d[x(i), x(j)] \leq r$)/(N−m+1);

$x(i) = [u(i), \ldots, u(i=m-1)]$;

$x(j) = [u(j), \ldots, u(j=m-1)]$;

$u(i), u(2) \ldots u(N)$ are time sequence data;

wherein N is the length of data cycle;

m is the number of data comparison;

r is a noise filtering coefficient;

In this example, the brain wave signal of the subject was analyzed with approximate entropy, and the result of which was used to predict further the depth of anesthesia of the subject. Low approximate entropy value indicated the anesthesia state of the subject, where the brain wave signal had a regularity and predictability. On the contrary, high approximate entropy value represented the irregularity and non-predictability of the brain wave signal from the subject, which in turn indicated that the subject was readily to regain consciousness.

The approximate entropy was calculated as follows:

$$\text{Approximat Entropy} = \Phi^m(r) - \Phi^{m+1}(r) \quad (1)$$

wherein
$\Phi^m(r)$ is defined as in the following formula (2):

$$\Phi^m(r) = (N - m + 1)^{-1} \cdot \sum_{i=1}^{N-m+1} \ln C_i^m(r) \quad (2)$$

$C_i^m(r)$ is defined as in the following formula (3):

$$C_i^m(r) = (\text{number of } x(j) \text{ such that } d[x(i),x(j)] \leq r)/(N-m+1) \quad (3)$$

x(i) and x(j) are defined as in the following formula (4):

$$x(i) = [u(i), \ldots, u(i-m-1)]$$

$$x(j) = [u(j), \ldots, u(j=m-1)] \quad (4)$$

u(i),u(2) ... u(N) represent the data of time sequence.

Referring to FIG. 2A number 17, a method for predicting the depth of anesthesia, comprising step 4: using a computer to compute corrected approximate entropy value by multiplying the approximate entropy value obtained in step 2 to 1000/17. In order to compare conveniently with other method, in this example, the value (0 to 1.7) of approximate entropy calculated as described above was set linearly within a range of 0 to 100. That is, the value of approximate entropy calculated originally was multiplied by 1000/17. Thus, the corrected approximate entropy value was used to represent the degree of conscious state, the depth of anesthesia or the degree of tranquilization of a subject. The approximate entropy value can also be divided into following 4 grades:

(1) 70-100: the subject is in a conscious state or slightly tranquilized state and is freely movable.
(2) 60-70: the subject is in a slight non-conscious state or gradually restoring the conscious state and the state occurred in a patient is just at the end of the operation but not regaining consciousness.
(3) 40-60: the subject is in a non-conscious state. In general, a patient undergoing an operation should be controlled within this range of depth of anesthesia, which indicates the optimal dosage range.
(4) 0-40: the subject is in an excessively non-conscious state. If the subject is a patient in an operation room, this indicates the over dosage of anesthetics that makes the depth of anesthesia of the patient being into excessively deep.

Finally, referring to FIG. 2A number 18, a method for predicting the depth of anesthesia, comprising step 5: displaying calculated corrected approximate entropy value on a monitor as the subject's the depth of anesthesia state.

Figure 2B:
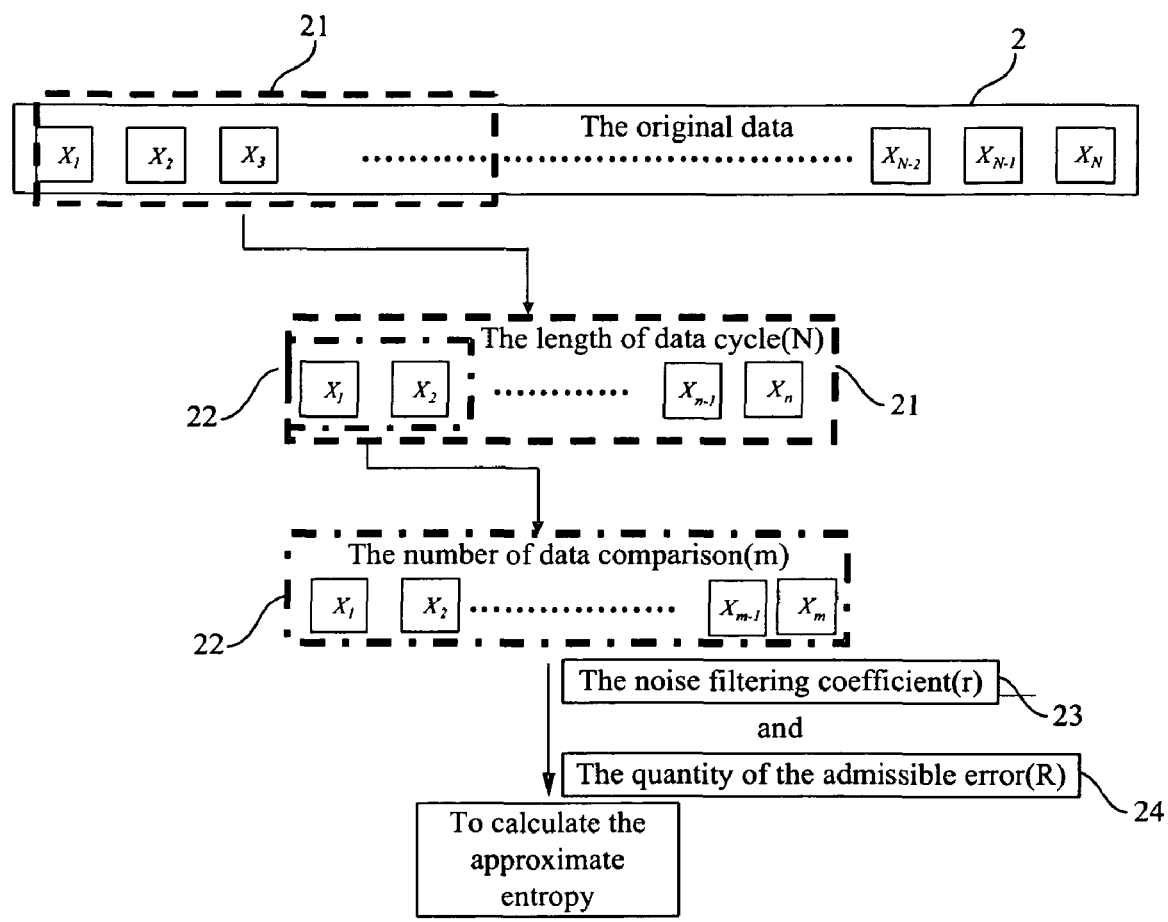
FIG. 2B is a flow chart illustrating the calculation of the approximate entropy.
Figures 1, 3:
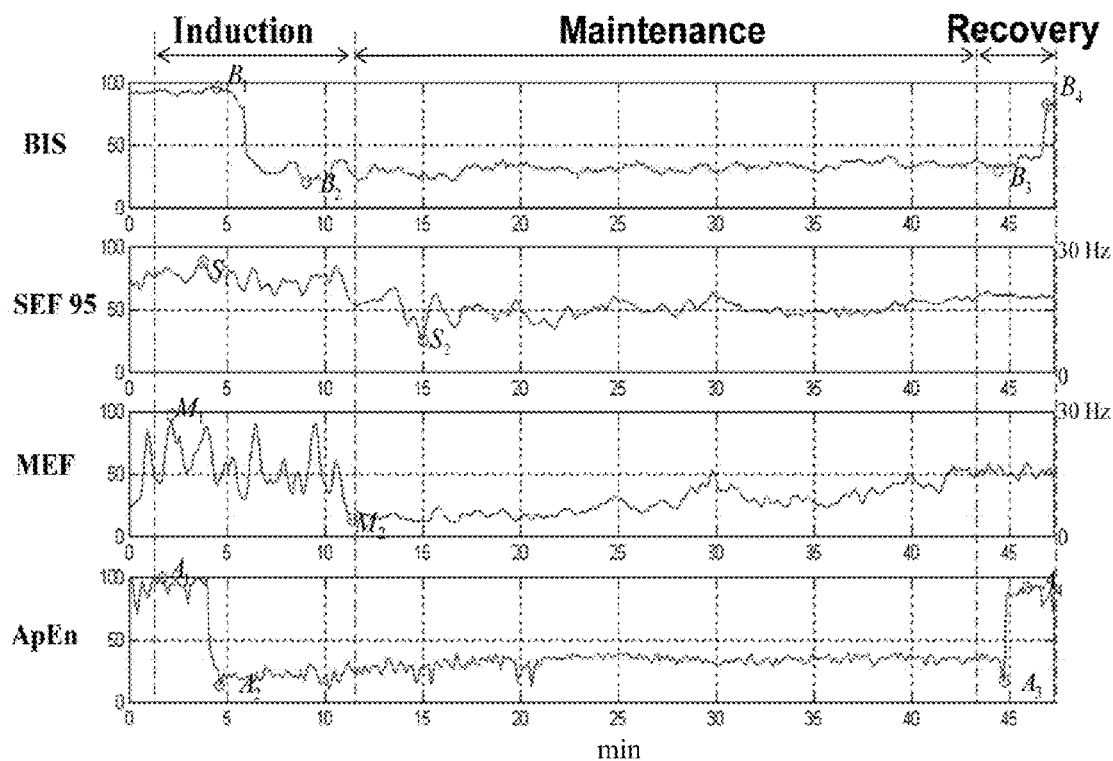
Figures 2, 3:
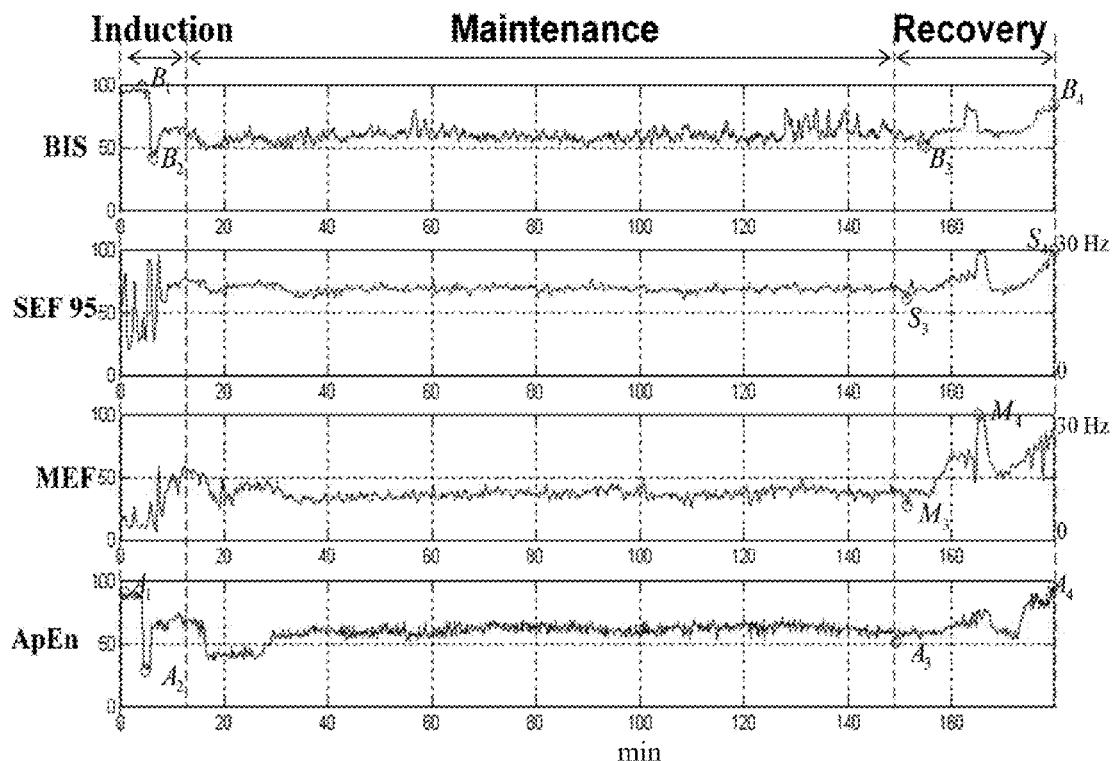
Figure 3:
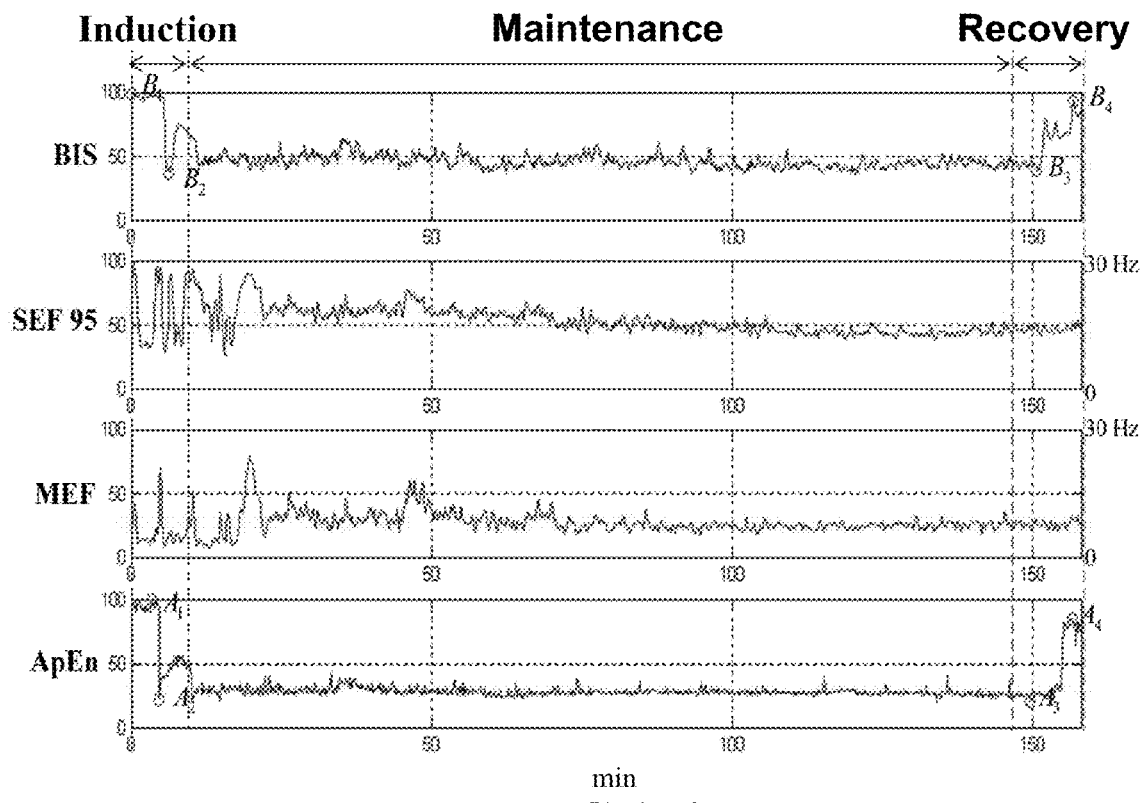
Figures 3, 4:
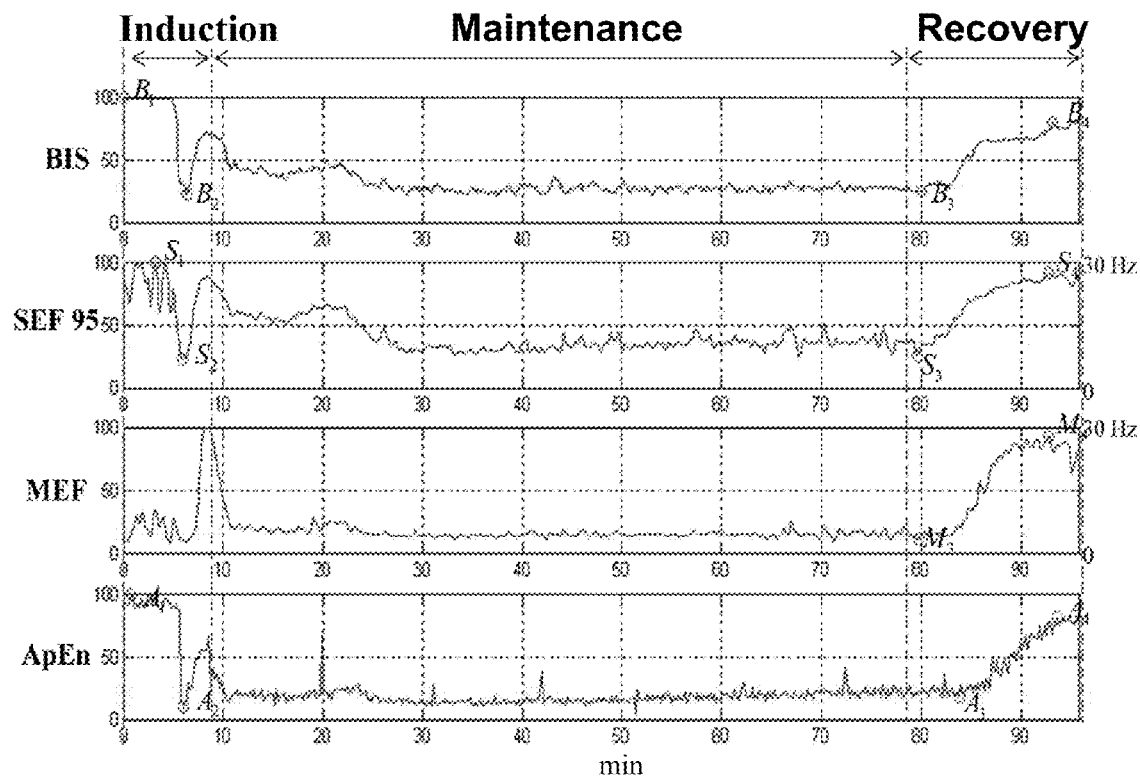
Figures 3, 4, 5:
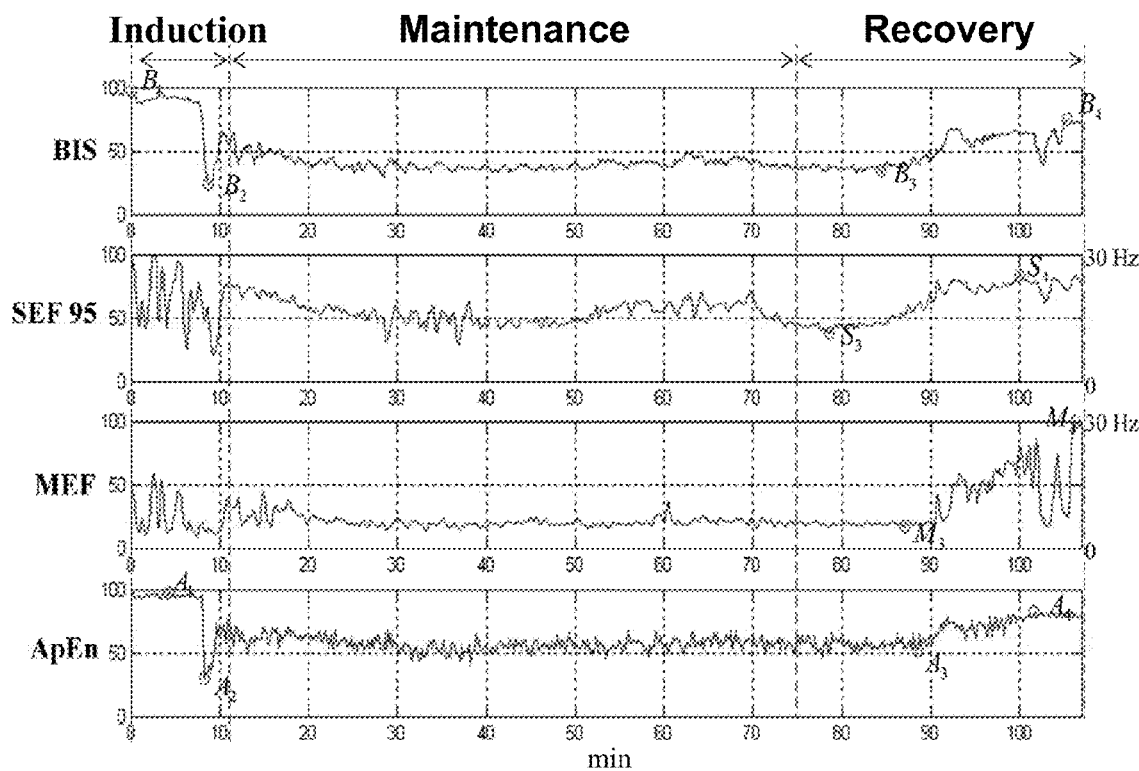
Figures 3, 4, 5, 6:
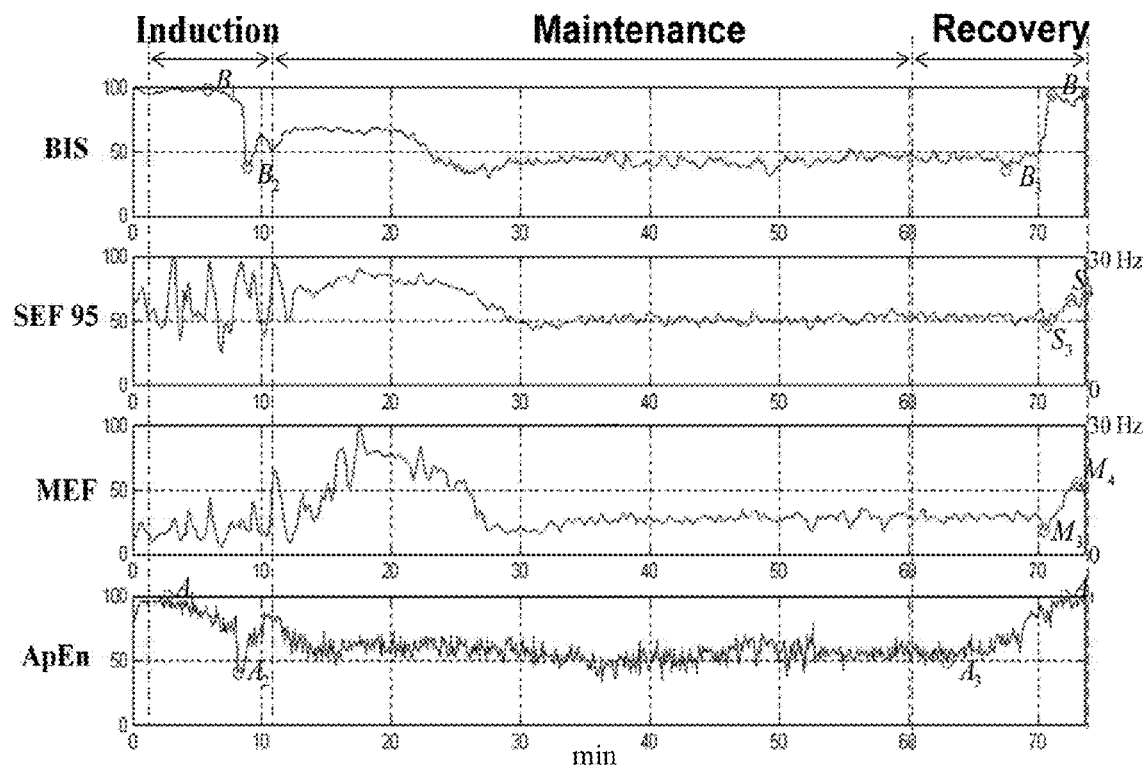
Figures 3, 4, 5, 6, 7:
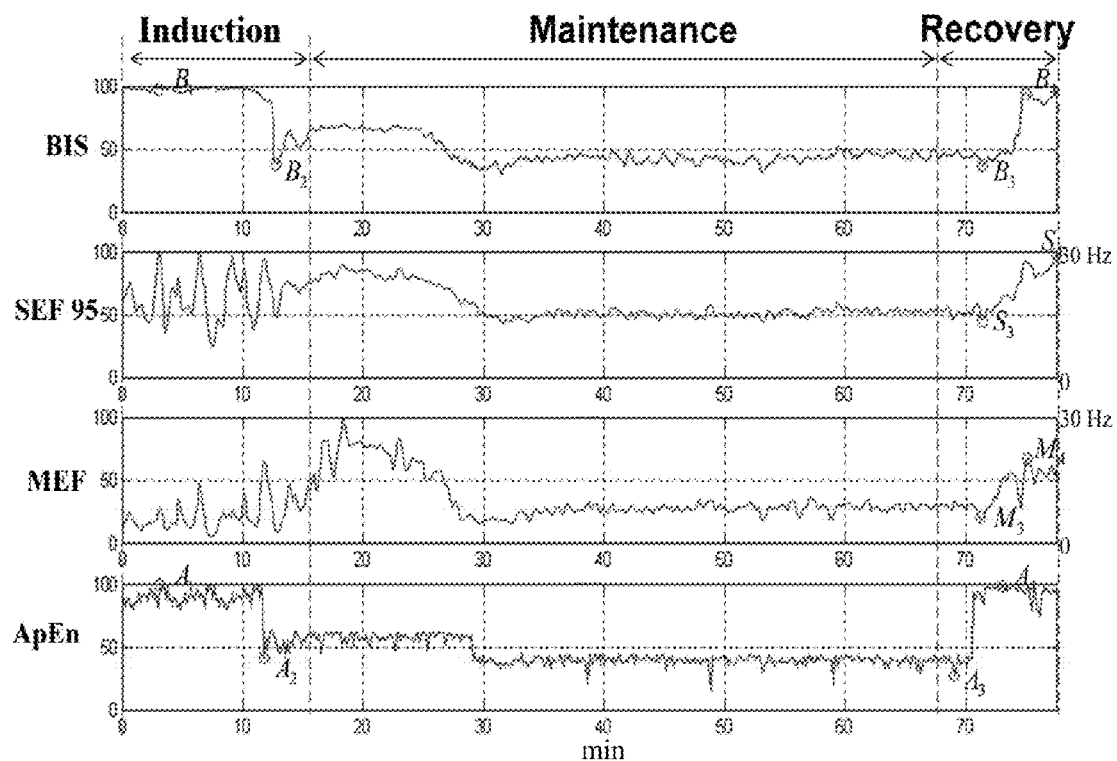
Figures 3, 4, 5, 6, 7, 8:
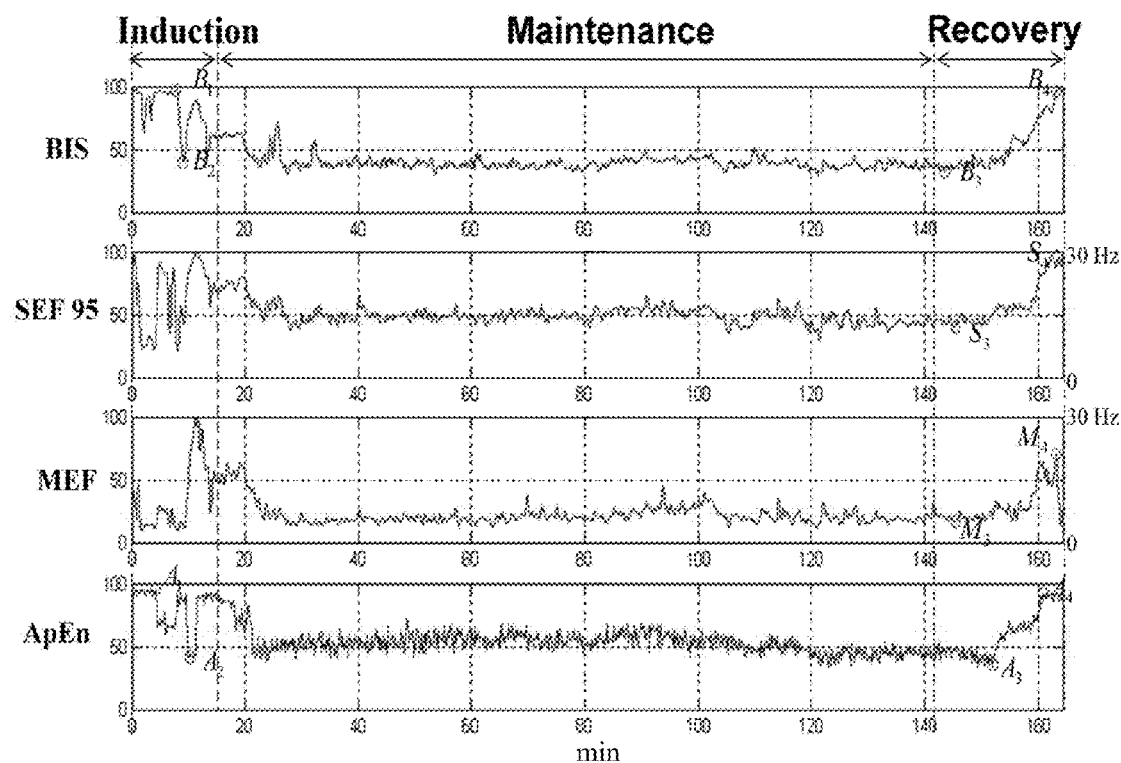
Figures 3, 4, 5, 6, 7, 8, 9:
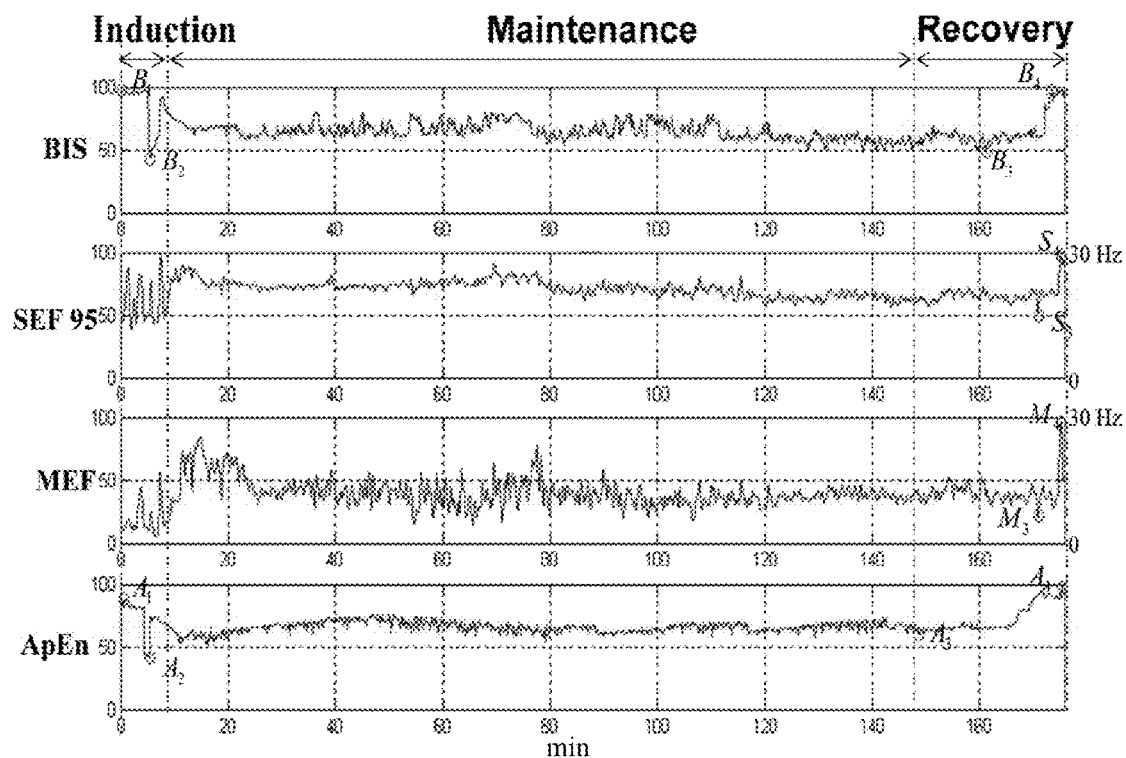
Figures 3, 4, 5, 6, 7, 8, 9, 10:
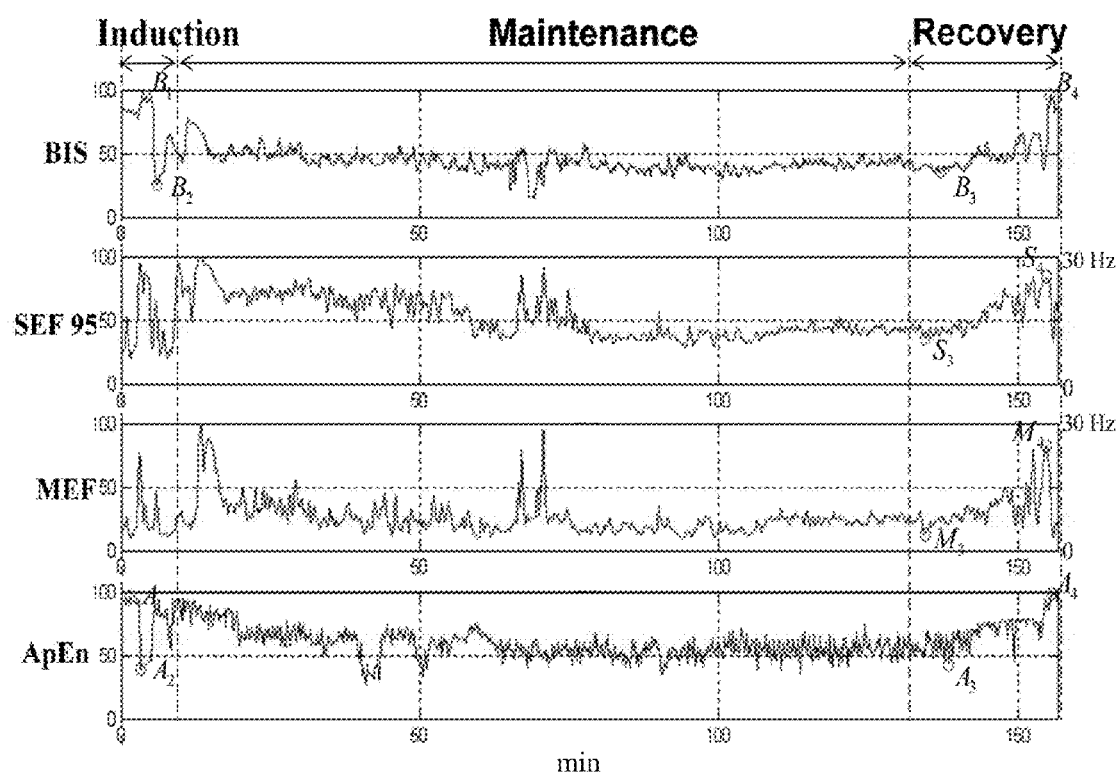
Figures 3, 4, 5, 6, 7, 8, 9, 10, 11:
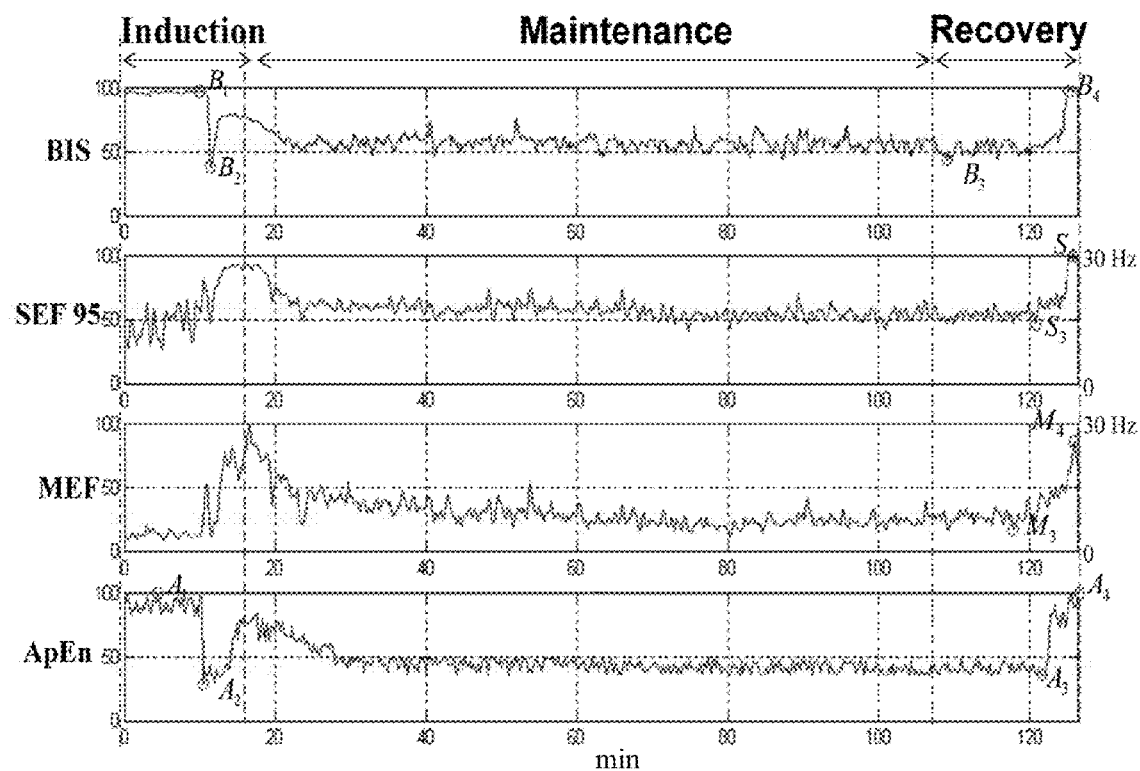
Figures 3, 4, 5, 6, 7, 8, 9, 10, 11, 12:
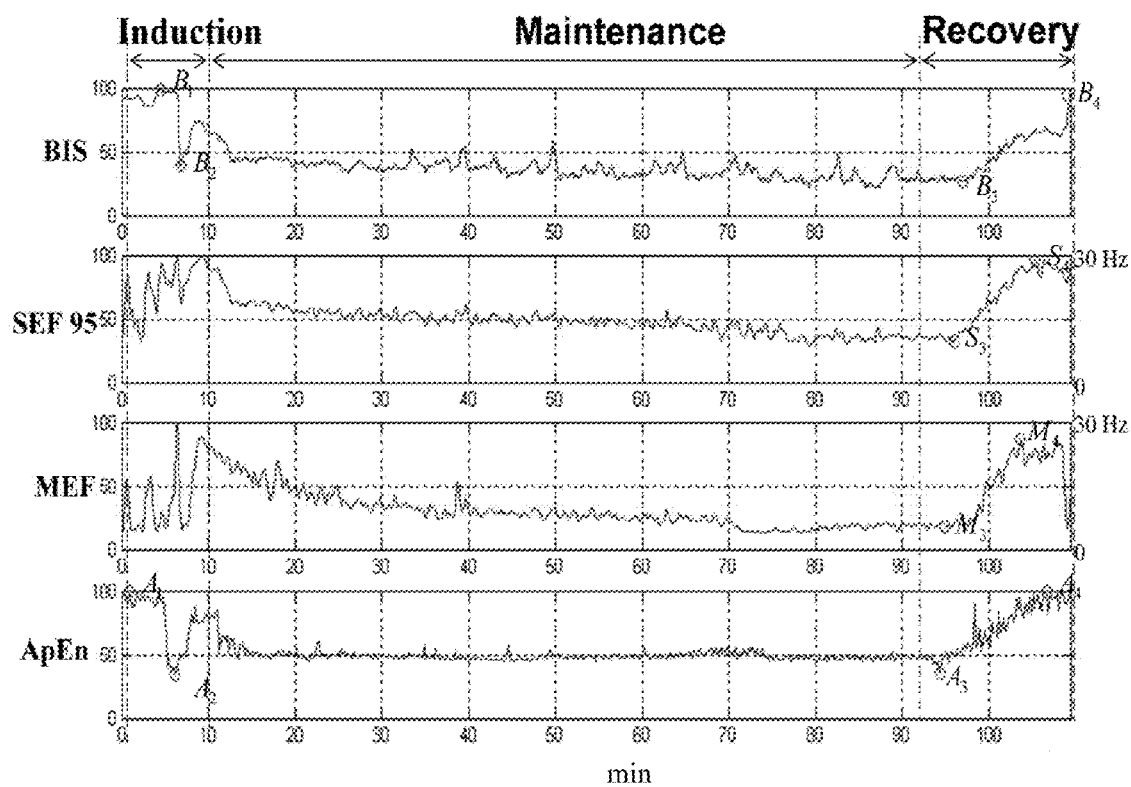
Figures 3, 4, 5, 6, 7, 8, 9, 10, 11, 12, 13:
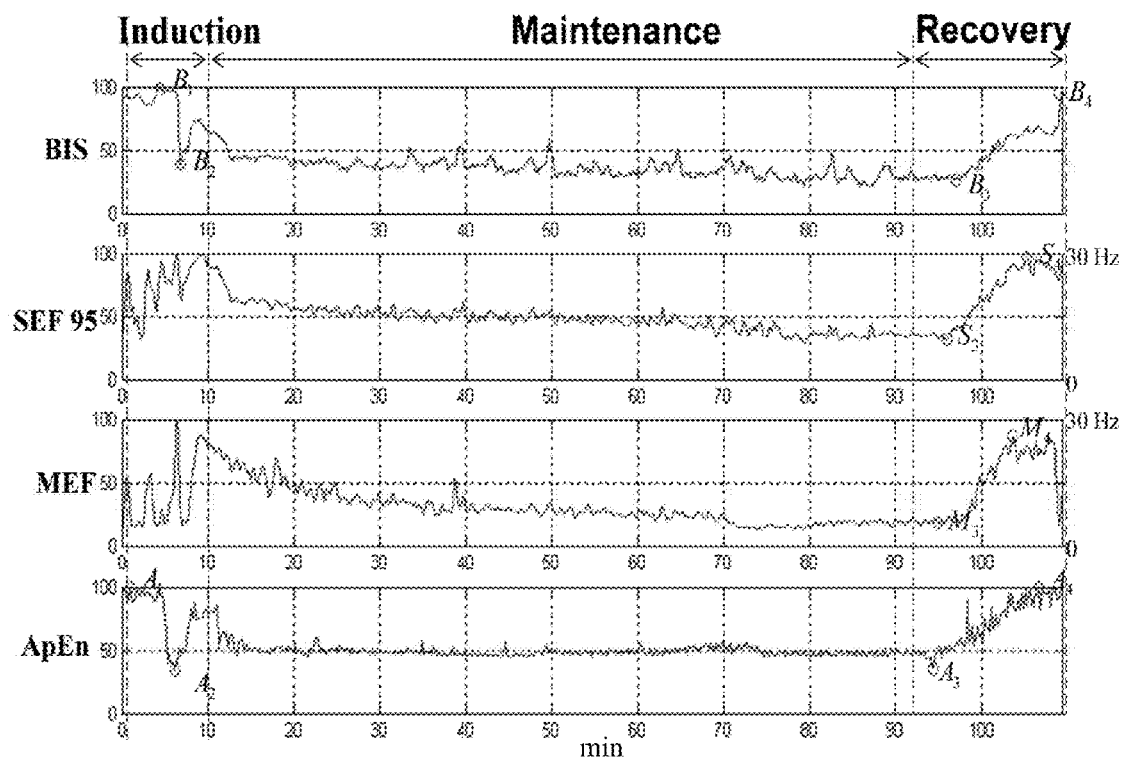
Figures 3, 4, 5, 6, 7, 8, 9, 10, 11, 12, 13, 14:
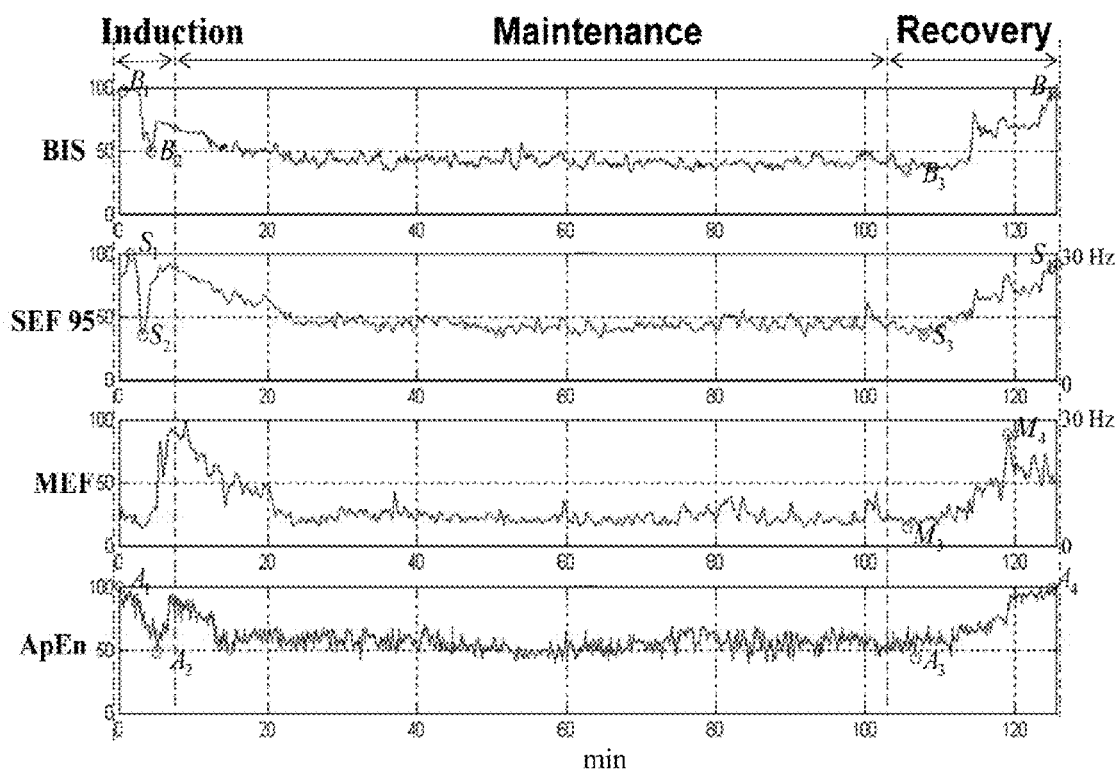
Figures 3, 4, 5, 6, 7, 8, 9, 10, 11, 12, 13, 14, 15:
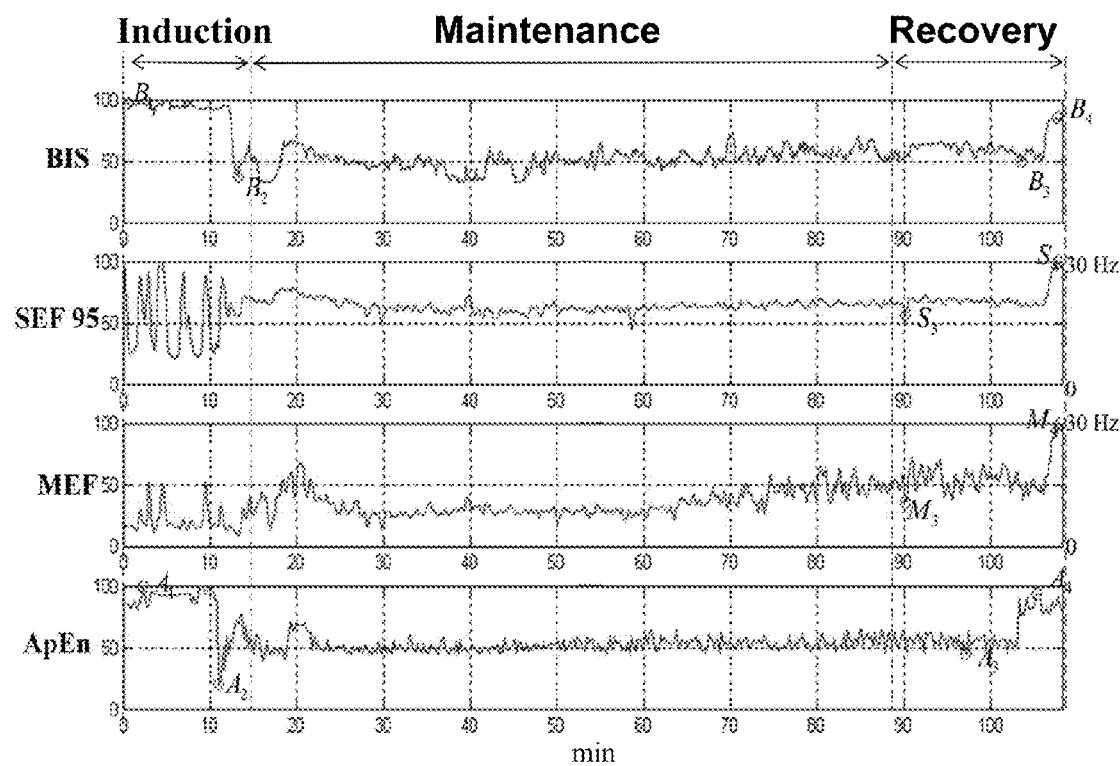
Figures 3, 4, 5, 6, 7, 8, 9, 10, 11, 12, 13, 14, 15, 16:
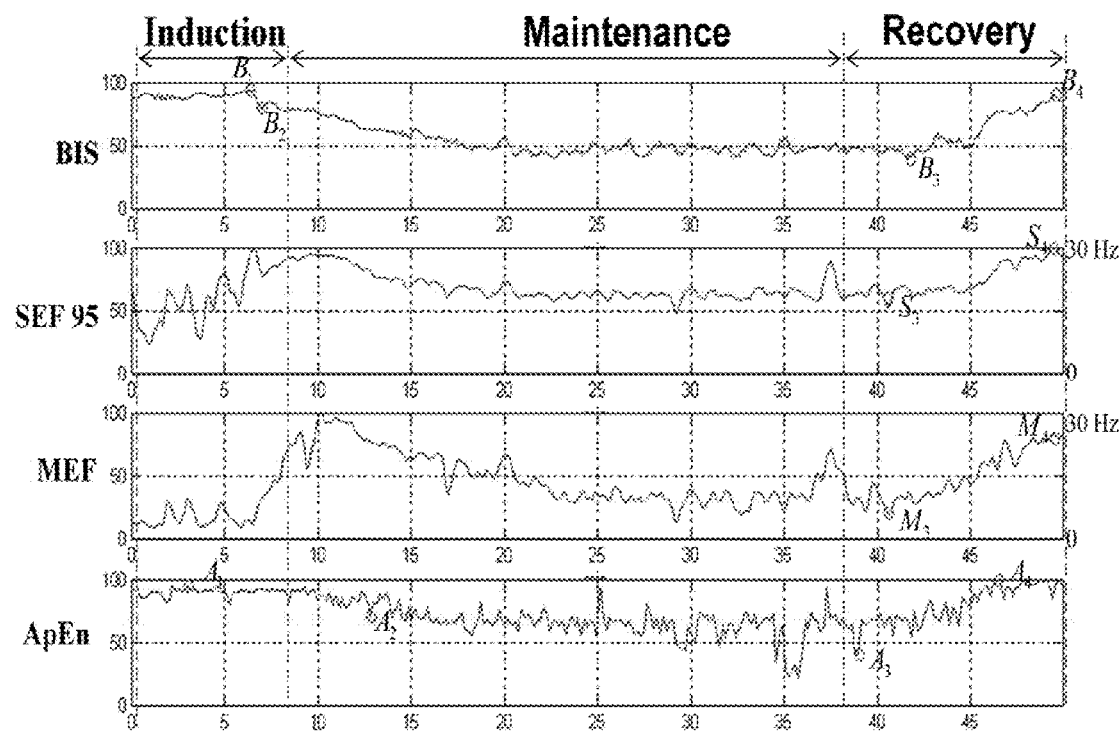
Figures 3, 4, 5, 6, 7, 8, 9, 10, 11, 12, 13, 14, 15, 16, 17:
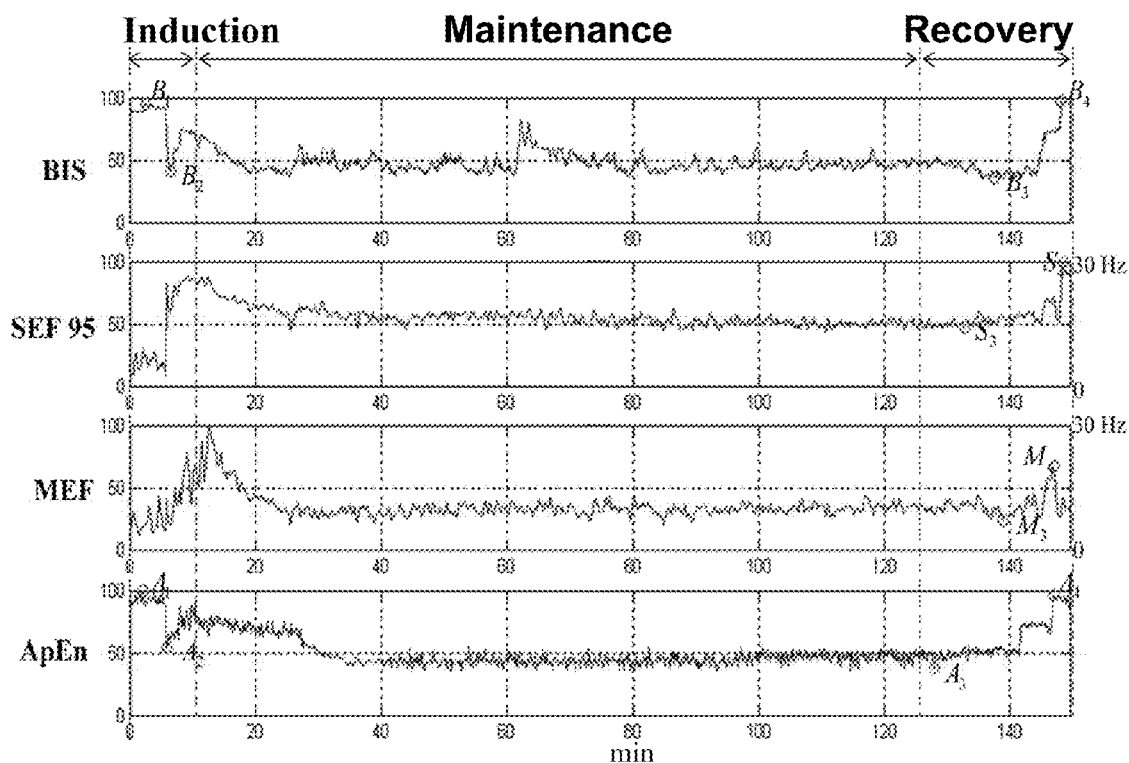
Figures 3, 4, 5, 6, 7, 8, 9, 10, 11, 12, 13, 14, 15, 16, 17, 18:
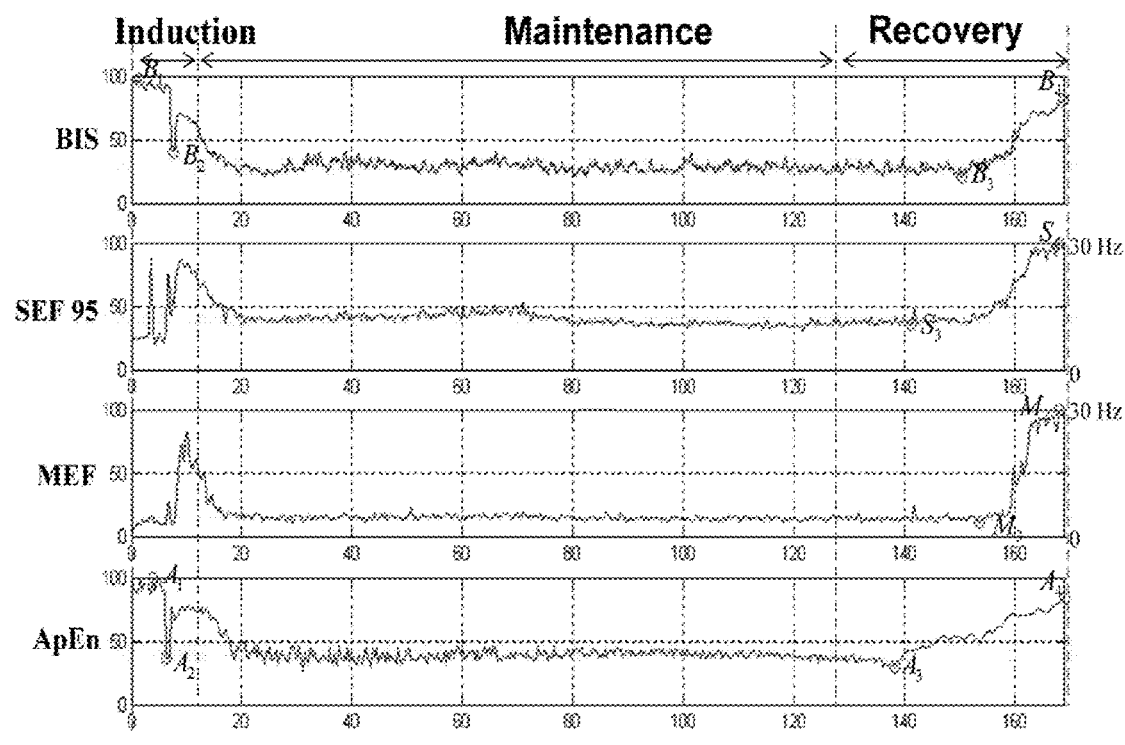
Figures 3, 4, 5, 6, 7, 8, 9, 10, 11, 12, 13, 14, 15, 16, 17, 18, 19:
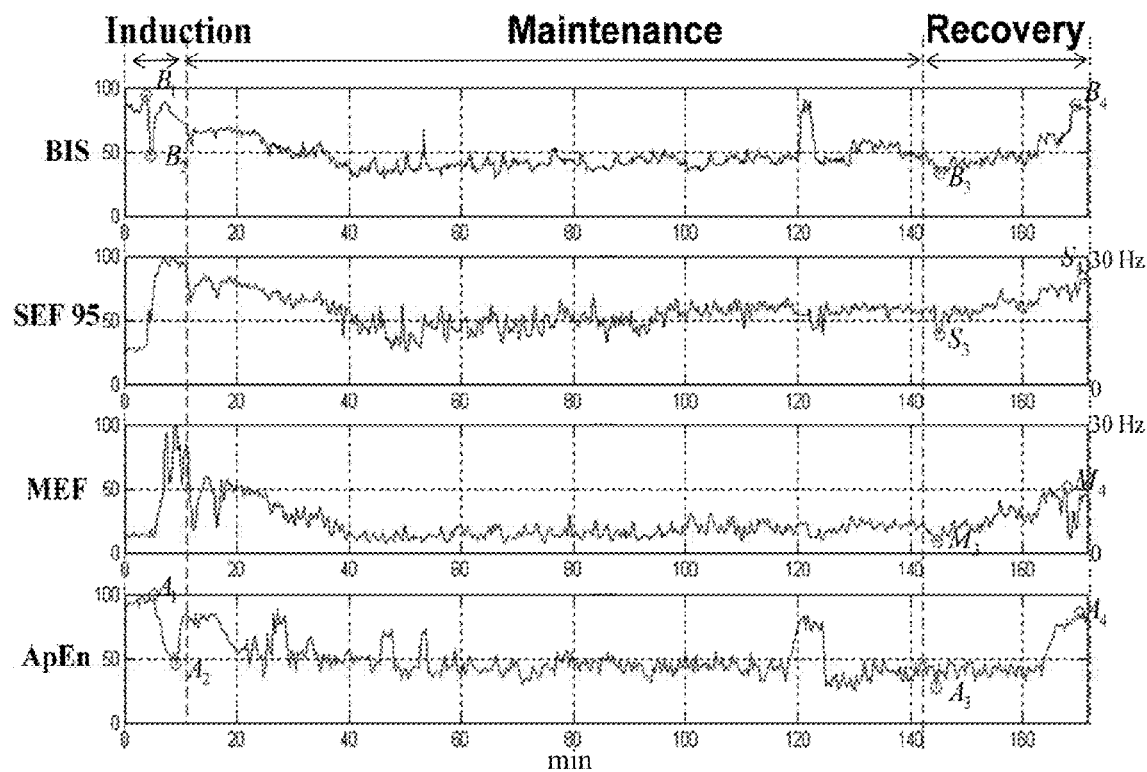
Figures 3, 4, 5, 6, 7, 8, 9, 10, 11, 12, 13, 14, 15, 16, 17, 18, 19, 20:
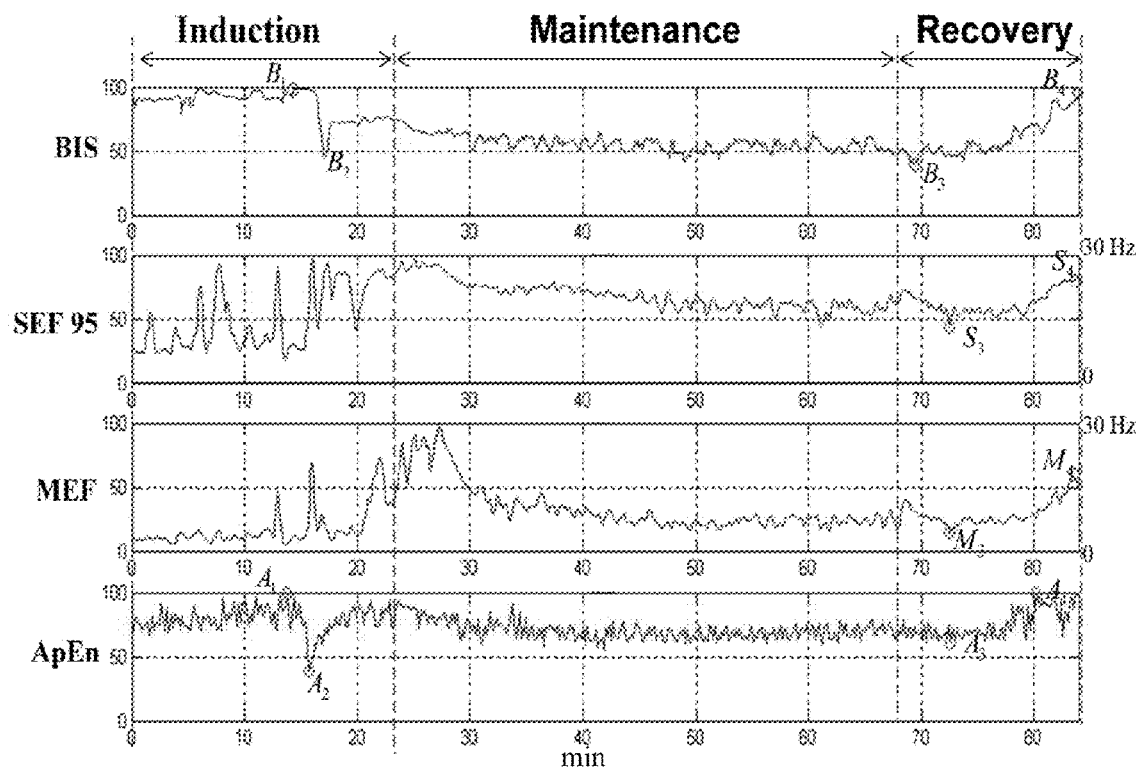
Figures 3, 4, 5, 6, 7, 8, 9, 10, 11, 12, 13, 14, 15, 16, 17, 18, 19, 20, 21:
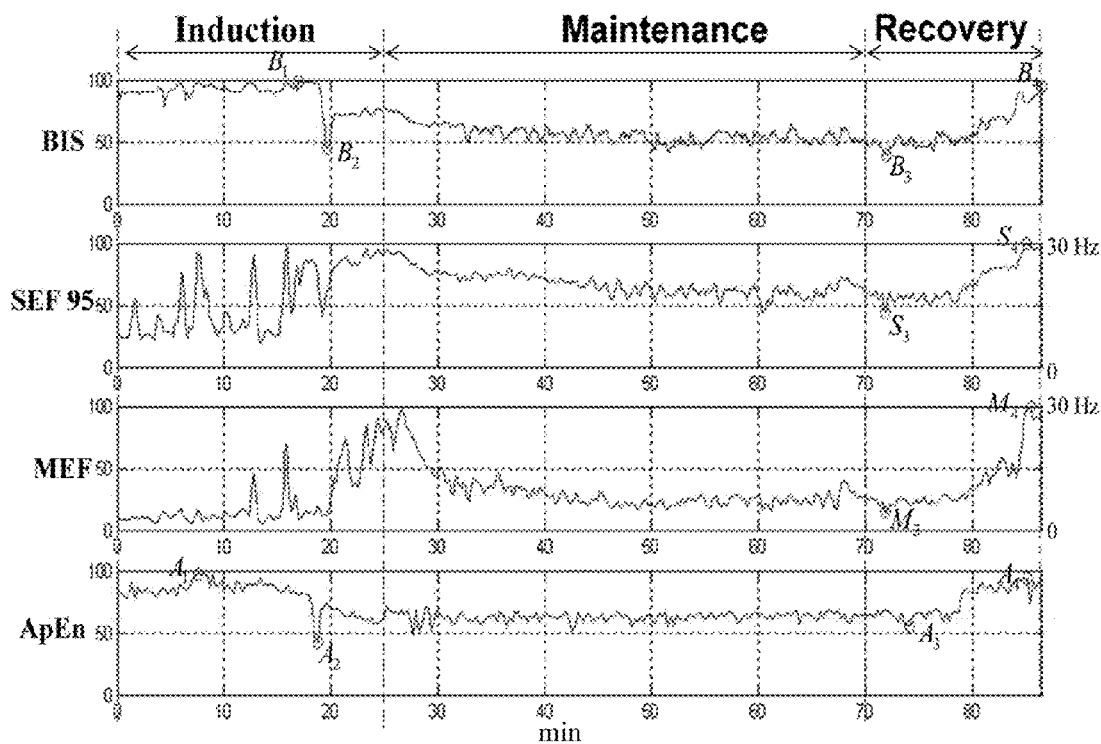
Figures 3, 4, 5, 6, 7, 8, 9, 10, 11, 12, 13, 14, 15, 16, 17, 18, 19, 20, 21, 22:
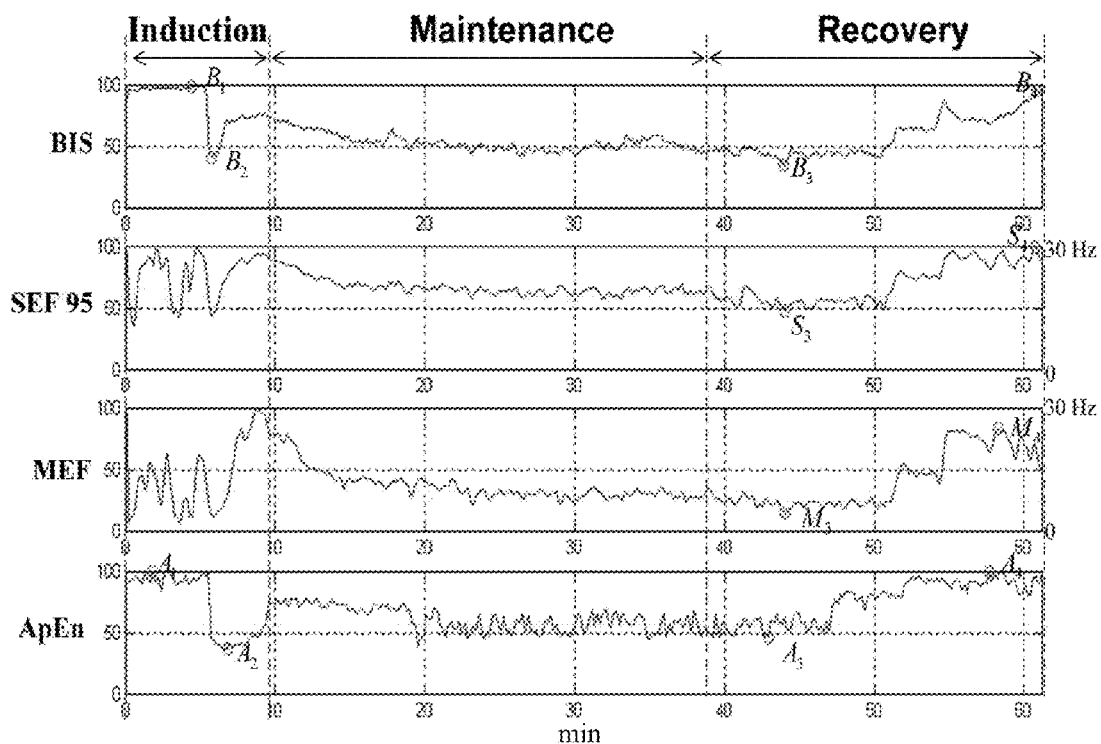
Figures 3, 4, 5, 6, 7, 8, 9, 10, 11, 12, 13, 14, 15, 16, 17, 18, 19, 20, 21, 22, 23:
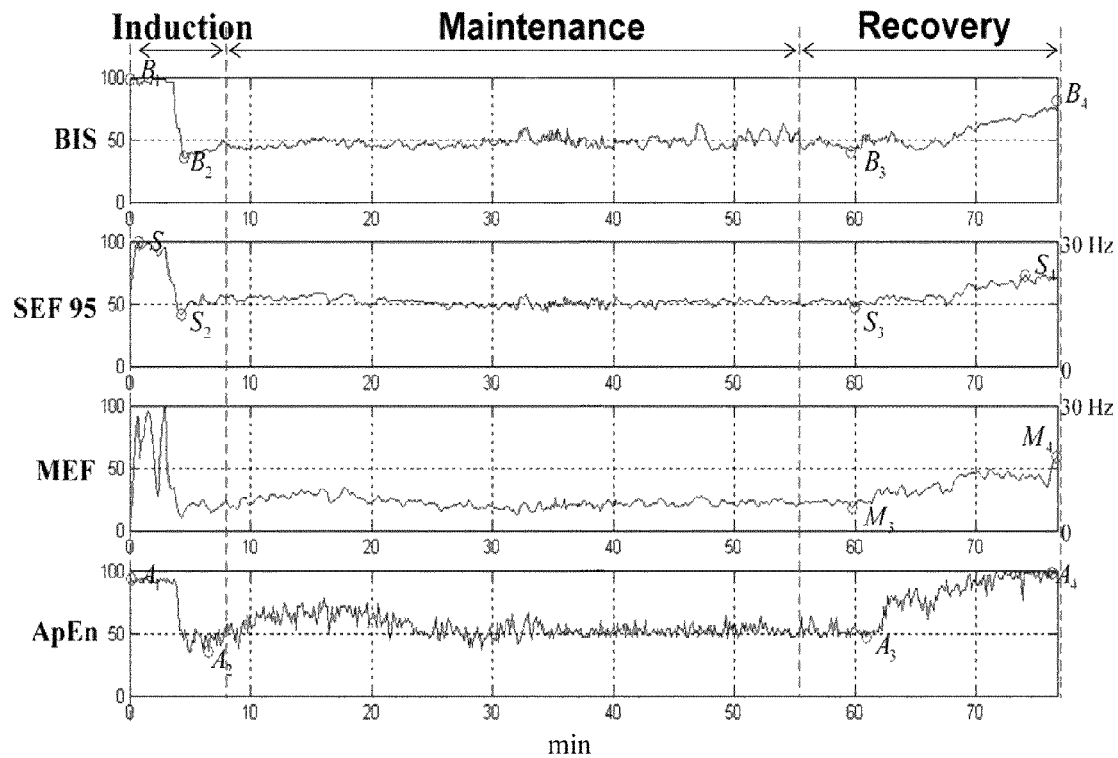
Figures 3, 4, 5, 6, 7, 8, 9, 10, 11, 12, 13, 14, 15, 16, 17, 18, 19, 20, 21, 22, 23, 24:
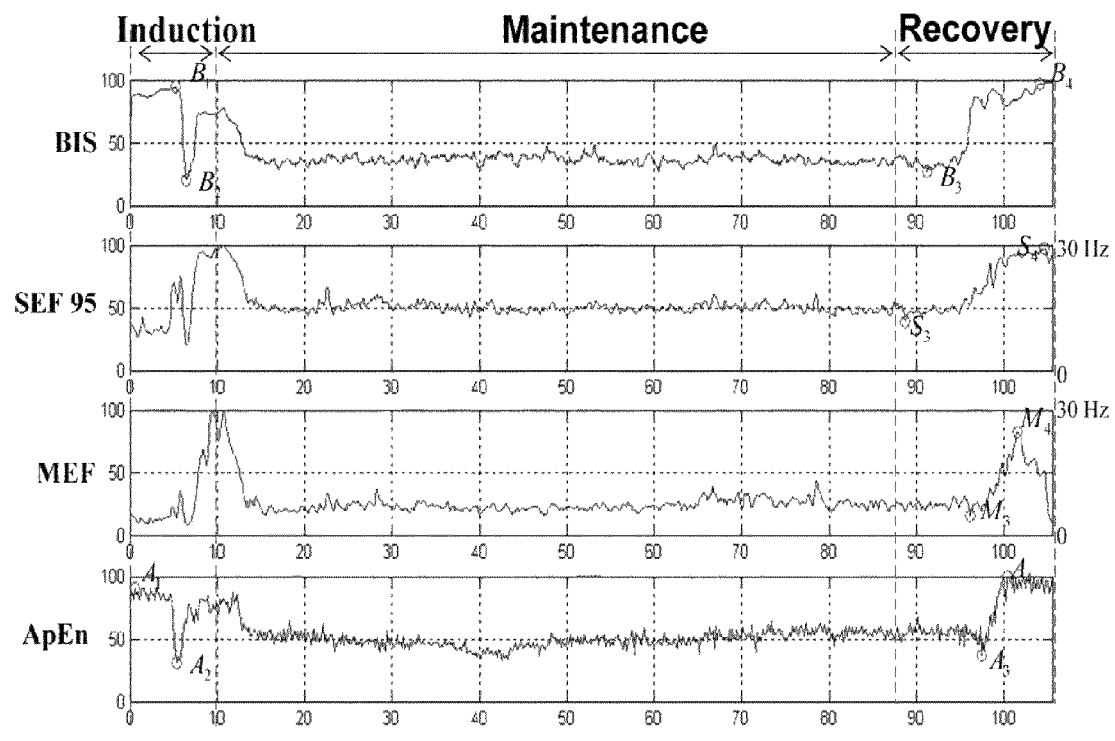
Figures 3, 4, 5, 6, 7, 8, 9, 10, 11, 12, 13, 14, 15, 16, 17, 18, 19, 20, 21, 22, 23, 24, 25:
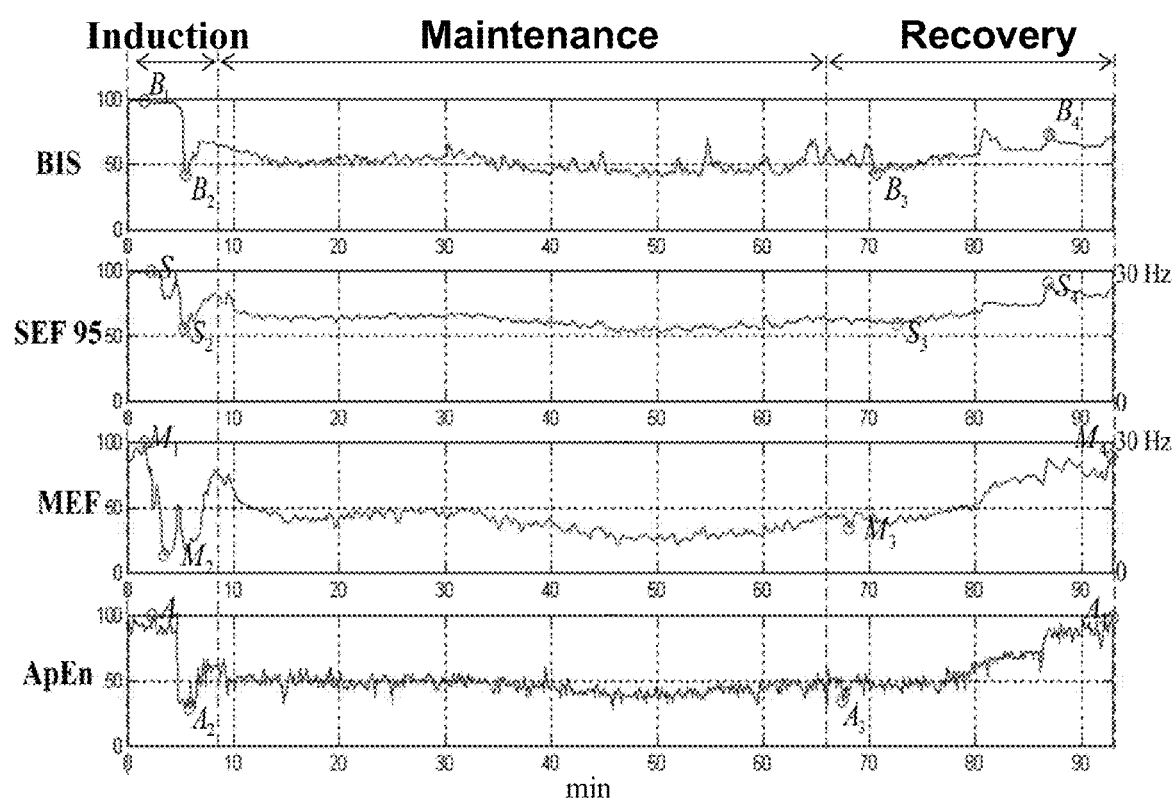

Irregularity calculated from approximate entropy value was deduced on the base of three parameters, i.e., the length of data cycle (N), the number of data comparison (m), and the noise filtering coefficient (r). These three parameters can be correlated as illustrated in FIG. 2B, and they are defined as follows:

(1) The length of data cycle (N) 21: It is derived from the segmentation of the original data 2. In the approximate entropy theory, the length of data cycle (N) 21 is defined as the sliding block of data analysis, and it is also one of the most important parameters that can affect the result. Since the approximate entropy theory calculates the regularity based on the difference between points within the time domain data, in case of too little set of the sliding block, data groups will be so deficient that the regularity cannot be predicted precisely. On the other hand, if the setting of the sliding block is too much, the precision of the analysis will be affected adversely due to the abundant duplicate data and lengthy analysis time.

(2) The number of data comparison (m) 22: It relates to the smaller data groups obtained by segmenting the above-mentioned length of data cycle (N) 21 with sliding blocks. In the approximate entropy theory, the number of data comparison (m) 22 is defined as the sliding block in the length of data cycle (N).

(3) The noise filtering coefficient (r) 23: The quantity of the admissible error (R) 24, which is among data points within each of various groups obtained from the segmentation of the data group, is defined by multiplying the noise filtering coefficient (r) by the standard deviation of the data.

In this example, set N=1024, m=2, r=0.2 for analyzing clinical data. In order to explain the step by step of how to calculate the approximate entropy, the following one group of $x_1$ to $x_{10}$ using approximate entropy for illustrating steps of approximate entropy analysis:

| $x_1$ | $x_2$ | $x_3$ | $x_4$ | $x_5$ | $x_6$ | $x_7$ | $x_8$ | $x_9$ | $x_{10}$ |
|---|---|---|---|---|---|---|---|---|---|
| 2 | 3 | 1 | 2 | 3 | 4 | 3 | 2 | 4 | 1 |

1. Step 1

The noise filtering coefficient (r) was assumed a value of 0, meaning that data points having a difference of 0 among them were data in coincidence with one another. The number of those coincidental data is referred as a match number. Next, the number of data comparison (m) was set as 1 and 2, and compared with all of the data sequence in m groups to obtain the match number.

(1) When m=1, the match number=3
   ($x_1 = x_1$; $x_1 = x_4$; $x_1 = x_8$)
(2) When m=2, match number=2
   ($x_1, x_2 = x_1, x_2$; $x_1, x_2 = x_4, x_5$)

2. Step 2

The process in Step 1 was repeated, while the number of data comparison (m) was set as m+1, and compared with all of the data sequence in m+1 group to obtain the match number.

(1) When m=1 was changed into m+1, the match number=2
   ($x_1, x_2 = x_1, x_2$; $x_1, x_2 = x_4, x_5$)
(2) When m=2 was changed into m+1, the match number=1
   ($x_1, x_2, x_3 = x_1, x_2, x_3$)

3. Step 3

The result obtained in Step 1 was divided by the result obtained in Step 2, and took logarithm, thereby the following result was yielded:
(1) When m=1, log(2/3) was obtained
(2) When m=2, log(1/2) was obtained 4. Step 4

The processes as described in Step 1, Step 2 and Step 3 were repeated, but using $x_1, x_2, x_3, x_4, x_5, x_6, x_7, x_8, x_9$ and $x_{10}$ as initial points, logarithms obtained in Step 3 were summed up, the sum thus yielded was divided by (N−m), and finally, the quotient was multiplied by −1. Values of approximate entropy (m, r, N) were thus obtained as follows:
(1) When m=1, the approximate entropy (1,0,10)

=−1[log(2/3)+log(1/3)+log(1/1)+log(2/3)+log(1/3)+log(1/2)+log(1/3)+log(1/3)+log(1/2)]/9

(2) When m=2, the approximate entropy (2,0,10)=

=−1[log(1/2)+log(1/1)+log(1/1)+log(1/2)+log(1/1)+log(1/1)+log(1/1)+log(1/1)]/8

Example 3

Results

FIG. 3-1 to 3-25 shows analytical value of BIS Index, SEF95, MEF, and approximate entropy obtained during the anesthesia period of the subject tested. Next, the anesthesia course was divided into three phases, i.e., induction, maintenance and recovery, and thereafter, the depth of anesthesia of the subject in each phase was analyzed using BIS Index, SEF95, MEF, and approximate entropy. Results were shown in Table 1, 2 and 3.

TABLE 1

The depth of anesthesia of the subject in induction phase of anesthesia using BIS Index, SEF95, MEF and approximate entropy

| Patient | BIS Index mean | BIS Index SD | SEF95 mean | SEF95 SD | MEF mean | MEF SD | ApEn mean | ApEn SD |
|---|---|---|---|---|---|---|---|---|
| 1 | 73.9 | 27.6 | 74.5 | 6.1 | 56.2 | 18 | 61.8 | 35.9 |
| 2 | 76.7 | 18.9 | 59.6 | 20.1 | 28.8 | 17.3 | 69.2 | 16.7 |
| 3 | 76.7 | 18.9 | 59.6 | 20.1 | 28.8 | 17.3 | 69.2 | 16.7 |
| 4 | 79.2 | 26.1 | 72.3 | 22.9 | 25.7 | 22.3 | 73.6 | 28.9 |
| 5 | 79.2 | 21.6 | 62.1 | 20.7 | 23.1 | 12.9 | 84.1 | 19.5 |
| 6 | 79.2 | 21.6 | 62.1 | 20.7 | 39.5 | 26.4 | 71.1 | 17.1 |
| 7 | 80.6 | 17.6 | 70.3 | 16.3 | 29.4 | 24.6 | 80.6 | 16.3 |
| 8 | 85.8 | 15.5 | 60.4 | 27.1 | 23.4 | 15.3 | 73.7 | 13.6 |
| 9 | 84.3 | 18.6 | 64.5 | 19.5 | 25.5 | 17.6 | 79.1 | 18.3 |
| 10 | 67.7 | 19.8 | 56.3 | 18 | 20.3 | 18.2 | 76.8 | 14.9 |
| 11 | 82.9 | 21.7 | 54.7 | 44.2 | 24.3 | 21.4 | 75.4 | 21.8 |
| 12 | 89.2 | 14.1 | 56.4 | 23.7 | 45.7 | 26.6 | 77.2 | 20.1 |
| 13 | 79.2 | 16.8 | 76.4 | 21.5 | 44.2 | 29.8 | 79.3 | 12.6 |
| 14 | 77.6 | 15.4 | 80.4 | 32.1 | 20.8 | 9.5 | 83.5 | 18.3 |
| 15 | 88.1 | 15.8 | 53.9 | 24.3 | 26.5 | 21 | 88.8 | 4.2 |
| 16 | 86.9 | 4.8 | 64.4 | 30.1 | 36.1 | 20 | 82.8 | 12.6 |
| 17 | 78 | 15.3 | 49.4 | 23.9 | 21.9 | 21.5 | 80.6 | 15.4 |
| 18 | 82.5 | 16.6 | 45.2 | 25.6 | 27.1 | 23.3 | 80.2 | 23.3 |
| 19 | 80.9 | 11.4 | 56.5 | 18.1 | 17.1 | 14.5 | 79.5 | 10.1 |
| 20 | 85.8 | 10.9 | 49.6 | 20.9 | 22.8 | 21.6 | 84.2 | 9.3 |
| 21 | 87.4 | 10.5 | 53.4 | 28.1 | 42.8 | 27.8 | 73.6 | 21.3 |
| 22 | 83.6 | 17.5 | 75.9 | 14.1 | 40.3 | 28.9 | 65.5 | 17.7 |
| 23 | 69.2 | 27.6 | 68.9 | 16.1 | 33.4 | 28.1 | 75.1 | 15.1 |
| 24 | 76.7 | 19.5 | 58.8 | 26.6 | 52.1 | 28.8 | 70.8 | 24.8 |
| 25 | 82.7 | 18.9 | 82.9 | 21.4 | 23.1 | 12.9 | 84.1 | 19.5 |
| Total average | 80.6 ± 5.5 | 17.7 ± 5.3 | 62.7 ± 10.1 | 22.5 ± 7.1 | 31.2 ± 10.6 | 21.0 ± 5.7 | 76.8 ± 6.5 | 17.8 ± 6.4 |
| CV | 0.07 | 0.30 | 0.16 | 0.32 | 0.34 | 0.27 | 0.08 | 0.34 |

TABLE 2

The depth of anesthesia of the subject in maintenance phase of anesthesia using BIS Index, SEF95, MEF and approximate entropy

| Patient | BIS Index mean | BIS Index SD | SEF95 mean | SEF95 SD | MEF mean | MEF SD | ApEn mean | ApEn SD |
|---|---|---|---|---|---|---|---|---|
| 1 | 29.5 | 6.0 | 40.6 | 6.8 | 15.9 | 6.8 | 40.1 | 6.7 |
| 2 | 46.5 | 10.7 | 56.2 | 12.6 | 22.0 | 13.5 | 46.9 | 12.1 |
| 3 | 54.6 | 5.8 | 68.6 | 24.1 | 33.9 | 10.6 | 69.7 | 6.2 |
| 4 | 55.7 | 6.8 | 65.9 | 9.4 | 30.8 | 15.4 | 62.9 | 3.8 |
| 5 | 46.7 | 4.2 | 51.8 | 2.8 | 23.2 | 4.4 | 53.7 | 6.6 |
| 6 | 46.7 | 4.2 | 51.8 | 2.8 | 23.2 | 4.4 | 53.7 | 6.6 |
| 7 | 37.4 | 5.5 | 51.1 | 7.1 | 24.9 | 8.0 | 50.6 | 7.5 |
| 8 | 50.9 | 5.2 | 61.5 | 4.5 | 38.8 | 9.0 | 46.1 | 5.8 |
| 9 | 31.2 | 4.3 | 52.3 | 8.1 | 30.3 | 13.3 | 31.5 | 5.8 |
| 10 | 59.5 | 5.2 | 68.6 | 36.9 | 36.9 | 4.3 | 59.0 | 6.4 |
| 11 | 59.5 | 5.2 | 68.6 | 36.9 | 36.9 | 4.3 | 59.0 | 6.4 |
| 12 | 30.9 | 8.7 | 40.5 | 12.4 | 17.2 | 10.0 | 18.8 | 5.8 |
| 13 | 39.7 | 4.6 | 53.3 | 8.8 | 20.5 | 4.1 | 57.0 | 5.1 |
| 14 | 43.3 | 5.7 | 55.0 | 9.9 | 31.4 | 13.6 | 56.4 | 7.1 |
| 15 | 43.6 | 6.3 | 53.2 | 7.7 | 29.1 | 9.3 | 40.2 | 5.5 |
| 16 | 40.4 | 7.2 | 50.2 | 8.8 | 23.2 | 10.5 | 52.6 | 8.5 |
| 17 | 64.6 | 6.6 | 70.1 | 6.1 | 39.9 | 10.1 | 65.4 | 3.9 |
| 18 | 42.3 | 6.3 | 51.5 | 14.8 | 25.5 | 11.5 | 58.2 | 10.3 |
| 19 | 49.3 | 8.1 | 61.2 | 7.3 | 35.3 | 12.7 | 50.0 | 9.0 |
| 20 | 56.8 | 5.9 | 57.9 | 8.5 | 30.5 | 12.9 | 44.6 | 7.9 |
| 21 | 35.7 | 6.6 | 48.9 | 8.8 | 29.1 | 12.8 | 49.4 | 4.2 |
| 22 | 42.8 | 6.2 | 46.8 | 9.8 | 26.6 | 13.0 | 55.9 | 7.1 |

TABLE 2-continued

The depth of anesthesia of the subject in maintenance phase of anesthesia using BIS Index, SEF95, MEF and approximate entropy

| Patient | BIS Index mean | SD | SEF95 mean | SD | MEF mean | SD | ApEn mean | SD |
|---|---|---|---|---|---|---|---|---|
| 23 | 52.7 | 8.3 | 64.4 | 4.6 | 38.3 | 12.3 | 52.8 | 5.7 |
| 24 | 51.1 | 8.9 | 67.7 | 9.8 | 46.6 | 20.2 | 64.6 | 11.6 |
| 25 | 47.3 | 6.5 | 54.8 | 6.4 | 34.7 | 9.2 | 48.5 | 9.5 |
| Total average | 46.3 ± 9.4 | 6.4 ± 1.6 | 56.5 ± 8.6 | 11.1 ± 8.9 | 29.8 ± 7.6 | 10.3 ± 4.1 | 51.5 ± 11.0 | 7.0 ± 2.2 |
| CV | 0.20 | 0.25 | 0.15 | 0.80 | 0.26 | 0.40 | 0.21 | 0.32 |

TABLE 3

The depth of anesthesia of the subject in recovery phase of anesthesia using BIS Index, SEF95, MEF and approximate entropy

| Patient | BIS Index mean | SD | SEF95 mean | SD | MEF mean | SD | ApEn mean | SD |
|---|---|---|---|---|---|---|---|---|
| 1 | 50.3 | 19.5 | 66.8 | 22.6 | 47.3 | 34.2 | 56.2 | 14.3 |
| 2 | 54.6 | 14.6 | 66.8 | 7.9 | 31.4 | 9.7 | 63.6 | 17.6 |
| 3 | 72.2 | 11.9 | 66.8 | 14.2 | 37.3 | 21.5 | 79.7 | 11.5 |
| 4 | 63.9 | 14.3 | 72.3 | 15.0 | 44.8 | 23.5 | 74.9 | 12.2 |
| 5 | 53.8 | 12.8 | 66.5 | 12.4 | 36.3 | 17.8 | 84.6 | 20.5 |
| 6 | 49.9 | 4.2 | 53.6 | 2.8 | 26.1 | 4.4 | 84.9 | 12.7 |
| 7 | 67.5 | 26.8 | 69.7 | 19.7 | 37.4 | 18.2 | 74.5 | 20.0 |
| 8 | 59.5 | 7.9 | 71.9 | 16.2 | 61.3 | 16.1 | 72.6 | 14.1 |
| 9 | 47.8 | 17.6 | 63.9 | 11.6 | 56.5 | 19.9 | 67.3 | 27.1 |
| 10 | 66.3 | 7.8 | 77.1 | 10.1 | 62.2 | 16.2 | 69.2 | 10.2 |
| 11 | 66.3 | 7.8 | 77.1 | 10.1 | 62.2 | 16.2 | 69.2 | 10.2 |
| 12 | 58.3 | 17.3 | 71.5 | 18.2 | 57.9 | 29.8 | 58.7 | 17.9 |
| 13 | 60.4 | 21.7 | 75.1 | 20.1 | 52.3 | 12.6 | 72.6 | 7.8 |
| 14 | 72.8 | 20.7 | 67.8 | 15.6 | 42.5 | 13.9 | 79.6 | 14.7 |
| 15 | 66.1 | 22.6 | 71.4 | 14.9 | 45.9 | 13.7 | 80.5 | 24.4 |
| 16 | 61.4 | 19.3 | 65.6 | 17.5 | 34.1 | 14.2 | 67.1 | 17.5 |
| 17 | 69.5 | 14.3 | 87.9 | 12.3 | 67.2 | 23.1 | 83.8 | 9.4 |
| 18 | 54.0 | 14.5 | 62.1 | 12.5 | 36.4 | 15.3 | 76.6 | 9.8 |
| 19 | 53.7 | 10.8 | 67.3 | 11.2 | 46.2 | 19.1 | 62.2 | 9.5 |
| 20 | 68.5 | 18.2 | 70.6 | 16.9 | 47.6 | 15.6 | 68.4 | 23.8 |
| 21 | 50.8 | 16.8 | 69.9 | 20.9 | 53.7 | 24.0 | 71.6 | 19.0 |
| 22 | 67.1 | 14.9 | 68.3 | 11.7 | 49.9 | 15.1 | 78.5 | 14.7 |
| 23 | 66.5 | 14.0 | 74.8 | 14.0 | 61.0 | 20.1 | 75.2 | 14.4 |
| 24 | 65.5 | 14.9 | 78.3 | 12.7 | 56.7 | 17.8 | 78.4 | 15.1 |
| 25 | 54.5 | 20.8 | 61.1 | 12.7 | 35.9 | 10.3 | 69.0 | 15.9 |
| Total average | 60.9 ± 7.6 | 15.4 ± 5.3 | 70.0 ± 6.7 | 14.2 ± 4.4 | 47.6 ± 11.3 | 17.7 ± 6.3 | 72.8 ± 7.8 | 15.4 ± 5.1 |
| CV | 0.13 | 0.34 | 0.10 | 0.31 | 0.24 | 0.36 | 0.11 | 0.33 |

Thereafter, variations of BIS Index, SEF95, MEF and approximate entropy in the induction and maintenance phases of anesthesia were compared in a quantitative manner. As results shown in Table 4, median values of difference between the induction and the maintenance phases of anesthesia obtained by each analytical method of BIS Index, SEF95, MEF, and approximate entropy were, 34.3, 4.5, −2.6 and 22.3, respectively.

Since values from these 4 types of analytical methods did not show normal distribution, a non-parametric statistical method of Kruskal Wallis Test was used to cross compare BIS Index, SEF95, MEF, and approximate entropy with one another in order to reveal whether there were significant differences in the anesthesia course among them. The obtained p value was less than 0.05, indicating that there were differences among these 4 analytical methods. Furthermore, a difference analysis of Mann-Whitney Rank Sum Test was conducted over results from these 4 analytical methods. As the result, p value for the difference between SEF95 and BIS Index, and between MEF and BIS Index, were less than 0.05, indicating both SEF95 and MEF had significant difference with BIS Index, and in addition, values of difference from these two methods were less than that of BIS Index. Consequently, both SEF95 and MEF failed to recognize effectively the course of consciousness change from conscious state to anesthetized state of the subject. FIG. 3-1 to 3-25 illustrated same results.

Conversely, p values for approximate entropy and BIS Index were more than 0.05, which indicated not only the analytical method based on approximate entropy was capable of predicting the course from conscious to anesthesia state of the subject as effectively as the analytical method based on BIS Index, but also its performance on the induction phase, like the analytical method based on BIS Index, exhibited no dramatic change just.

TABLE 4

Values of difference between induction and maintenance phases of anesthesia obtained using varioius analytical methods
Induction - Maintenance

| Patient | BIS | SEF95 | MEF | ApEn |
|---|---|---|---|---|
| 1 | 44.4 | 33.9 | 40.3 | 21.7 |
| 2 | 30.2 | 3.4 | 6.8 | 22.3 |
| 3 | 22.1 | −9 | −5.1 | −0.5 |
| 4 | 23.5 | 6.4 | −5.1 | 10.7 |
| 5 | 32.5 | 10.3 | −0.1 | 30.4 |
| 6 | 32.5 | 10.3 | 16.3 | 17.4 |
| 7 | 43.2 | 19.2 | 4.5 | 30 |
| 8 | 34.9 | −1.1 | −15.4 | 27.6 |
| 9 | 53.1 | 12.2 | −4.8 | 47.6 |
| 10 | 8.2 | −12.3 | −16.6 | 17.8 |
| 11 | 23.4 | −13.9 | −12.6 | 16.4 |
| 12 | 58.3 | 15.9 | 28.5 | 58.4 |
| 13 | 39.5 | 23.1 | 23.7 | 22.3 |
| 14 | 34.3 | 25.4 | −10.6 | 27.1 |
| 15 | 44.5 | 0.7 | −2.6 | 48.6 |
| 16 | 46.5 | 14.2 | 12.9 | 30.2 |
| 17 | 13.4 | −20.7 | −18 | 15.2 |
| 18 | 40.2 | −6.3 | 1.6 | 22 |
| 19 | 31.6 | −4.7 | −18.2 | 29.5 |
| 20 | 29 | −8.3 | −7.7 | 39.6 |
| 21 | 51.7 | 4.5 | 13.7 | 24.2 |
| 22 | 40.8 | 29.1 | 13.7 | 9.6 |
| 23 | 16.5 | 4.5 | −4.9 | 22.3 |
| 24 | 25.6 | −8.9 | 5.5 | 6.2 |
| 25 | 35.4 | 28.1 | −11.6 | 35.6 |
| Median | 34.3 | 4.5 | −2.6 | 22.3 |
| Range | (8.2, 52.3) | (−20.7, 33.9) | (−18.2, 40.3) | (−0.5, 58.4) |

BIS vs. SEF95 vs. MEF vs. ApEn, $p < 0.05$ using Kruskal Wallis Test
BIS vs. SEF95, $p < 0.05$ using Mann-Whitney Rank Sum Test
BIS vs. MEF, $p < 0.05$ using Mann-Whitney Rank Sum Test
BIS vs. ApEn, $p > 0.05$ using Mann-Whitney Rank Sum Test During the recovery phase of anesthesia, the conscious state of the subject would regain consciousness gradually from coma. Therefore, a quantitative method was used further to compare changes of BIS Index, SEF95, MEF, and approximate entropy during the recovery and the maintenance phases of anesthesia. Results in Table 5 indicated that median values of the difference between the recovery and the maintenance phases of anesthesia obtained by various analytical methods were 13.8, 11.6, 16.8 and 20.5, respectively. These medium values in top-down order were successively as approximate entropy, MEF, BIS Index, and SEF95.

Since values from these 4 types of analytical methods did not show normal distribution, a non-parametric statistical method of Kruskal Wallis Test was used to cross compare BIS Index, SEF95, MEF, and approximate entropy with one another in order to reveal whether there were significant differences in the anesthesia course among them. The obtained p value was less than 0.05, indicating that there were differences among these 4 analytical methods. Furthermore, a difference analysis of Mann-Whitney Rank Sum Test was conducted over results from these 4 analytical methods. As the result, p value for the difference between SEF95 and BIS Index, and between MEF and BIS Index, were more than 0.05, indicating both SEF95 and MEF were, like BIS Index, capable of predicting the course from anesthesia to conscious state of the subject.

In addition, p values for approximate entropy and BIS were less than 0.05, and the median value of approximate entropy is higher than the median value of BIS Index. This indicated approximate entropy was more effective than BIS Index in predicting the course from maintenance to anesthesia phases of the subject.

TABLE 5

Value of difference between recovery and maintenance phases of anesthesia obtained using various analytical methods
Recovery - Maintenance

| Patient | BIS | SEF95 | MEF | ApEn |
|---|---|---|---|---|
| 1 | 20.8 | 26.2 | 31.4 | 16.1 |
| 2 | 8.1 | 10.6 | 9.4 | 16.7 |
| 3 | 17.6 | −1.8 | 3.4 | 10 |
| 4 | 8.2 | 6.4 | 14 | 12 |
| 5 | 7.1 | 14.7 | 13.1 | 30.9 |
| 6 | 3.2 | 1.8 | 2.9 | 31.2 |
| 7 | 30.1 | 18.6 | 12.5 | 23.9 |
| 8 | 8.6 | 10.4 | 22.5 | 26.5 |
| 9 | 16.6 | 11.6 | 26.2 | 35.8 |
| 10 | 6.8 | 8.5 | 25.3 | 10.2 |
| 11 | 6.8 | 8.5 | 25.3 | 10.2 |
| 12 | 27.4 | 31 | 40.7 | 39.9 |
| 13 | 20.7 | 21.8 | 31.8 | 15.6 |
| 14 | 29.5 | 12.8 | 11.1 | 23.2 |
| 15 | 22.5 | 18.2 | 16.8 | 40.3 |
| 16 | 21 | 15.4 | 10.9 | 14.5 |
| 17 | 4.9 | 17.8 | 27.3 | 18.4 |
| 18 | 11.7 | 10.6 | 10.9 | 18.4 |
| 19 | 4.4 | 6.1 | 10.9 | 12.2 |
| 20 | 11.7 | 12.7 | 17.1 | 23.8 |
| 21 | 15.1 | 21 | 24.6 | 22.2 |
| 22 | 24.3 | 21.5 | 23.3 | 22.6 |
| 23 | 13.8 | 10.4 | 22.7 | 22.4 |
| 24 | 14.4 | 10.6 | 10.1 | 13.8 |
| 25 | 7.2 | 6.3 | 1.2 | 20.5 |
| Median | 13.8 | 11.6 | 16.8 | 20.5 |
| Range | (3.2, 30.1) | (−1.8, 31) | (1.2, 40.7) | (10, 40.3) |

BIS vs. SEF95 vs. MEF vs. ApEn, $p < 0.05$ using Kruskal Wallis Test
BIS vs. SEF95, $p > 0.05$ using Mann-Whitney Rank Sum Test
BIS vs. MEF, $p > 0.05$ using Mann-Whitney Rank Sum Test
BIS vs. ApEn, $p < 0.05$ using Mann-Whitney Rank Sum Test Next, after intravenous injecting the subject with thiopental, the sensitivities to the drug of these 4 analytical methods, i.e. those based on BIS Index, SEF95, MEF, and approximate entropy, respectively, were compared with one another. As the subject entered the induction phase of anesthesia, the slope of the line from the minimum value to the maximum value of the depth of anesthesia obtained from each analytical method was used to determine the sensitivity of the respective analytical theory to the drug. For this, the maximum value of depth of anesthesia from BIS Index was assumed to be $B_1$, while its minimum value was assumed to be $B_2$. The maximum value of depth of anesthesia from SEF95 was assumed to be $S_1$, while its minimum value was assumed to be $S_2$. The maximum value of depth of anesthesia from MEF was assumed to be $M_1$, while its minimum value was assumed to be $M_2$. The maximum value of depth of anesthesia from approximate entropy was assumed to be $A_1$, while its minimum value was assumed to be $A_2$. Values of $B_1$, $B_2$, $S_1$, $S_2$, $M_1$, $M_2$, $A_1$ and $A_2$ were shown in FIG. 3-1 to 3-25. Thereafter, the difference between the time at each point of the above-described $B_1$, $B_2$, $S_1$, $S_2$, $M_1$, $M_2$, $A_1$ and $A_2$ and the time the induction phase of anesthesia started was defined as the relative time. The relative time of each analytical method was expressed as BIS($B_1'$, $B_2'$), SEF95($S_1'$, $S_2$), MEF($M_1'$, $M_2'$), and approximate entropy ($A_1'$, $A_2'$). Then, the sensitivity of each of these 4 analytical methods to the brain wave change was compared using the slope between two points. The result was shown in Table 6.

TABLE 6

Comparison among sensitivities of BIS Index, SEF95, MEF and approximate entropy to the induction phase of anesthesia

| Patient | BIS | | | SEF95 | | | MEF | | | ApEn | | |
|---|---|---|---|---|---|---|---|---|---|---|---|---|
| | $B_1'$ | $B_2'$ | slope | $S_1'$ | $S_2'$ | slope | $M_1'$ | $M_2'$ | slope | $A_1'$ | $A_2'$ | slope |
| 1 | 4.5(96) | 9.1(9) | −16.7 | 3.8(88) | 15(26) | −5.5 | 2.2(97) | 11.4(13) | −9.1 | 1.7(100) | 4.6(13) | −29.9 |
| 2 | 4.2(98) | 5.4(20) | −28.3 | N/A | N/A | N/A | N/A | N/A | N/A | 0.9(90) | 4.9(29) | −15.1 |
| 3 | 0.2(98) | 6.2(37) | −10.1 | N/A | N/A | N/A | N/A | N/A | N/A | 3.5(100) | 4.7(22) | −65 |
| 4 | 1(100) | 6.3(23) | −12.3 | 3.3(100) | 6(23) | −29.1 | N/A | N/A | N/A | 0.8(100) | 6(10) | −17.1 |
| 5 | 1(97) | 8.8(24) | −8.4 | N/A | N/A | N/A | N/A | N/A | N/A | 4.3(97) | 8.3(30) | −16.5 |
| 6 | 5.8(98) | 8.8(38) | −20 | N/A | N/A | N/A | N/A | N/A | N/A | 0.5(96) | 5.4(20) | −11 |
| 7 | 3(98) | 13(38) | −6.1 | N/A | N/A | N/A | N/A | N/A | N/A | 3.1(100) | 12(41) | −6.8 |
| 8 | 7.8(98) | 9.1(40) | −43.1 | N/A | N/A | N/A | N/A | N/A | N/A | 4.2(97) | 10(41) | −9.1 |
| 9 | 1(98) | 5.5(43) | −10.1 | N/A | N/A | N/A | N/A | N/A | N/A | 1(88) | 5.3(41) | −10 |
| 10 | 4.3(95) | 6(25) | −40 | N/A | N/A | N/A | N/A | N/A | N/A | 2(96) | 3.3(39) | −31.2 |
| 11 | 2.7(98) | 8.7(31) | −11.2 | N/A | N/A | N/A | N/A | N/A | N/A | 6.6(95) | 7.8(34) | −56.8 |
| 12 | 10(98) | 11.4(38) | −42 | N/A | N/A | N/A | N/A | N/A | N/A | 4.5(99) | 10.5(29) | −11.7 |
| 13 | 5(98) | 6.8(39) | −25.6 | N/A | N/A | N/A | N/A | N/A | N/A | 1(99) | 6(34) | −12.7 |
| 14 | 1(98) | 4.3(50) | −12.7 | 1.7(100) | 3.3(36) | −40.7 | N/A | N/A | N/A | 1(100) | 5(48) | −10.5 |
| 15 | 1(97) | 13(38) | −4.6 | N/A | N/A | N/A | N/A | N/A | N/A | 2.3(100) | 5.4(20) | −9.1 |
| 16 | 6.4(94) | 7(80) | −20.8 | N/A | N/A | N/A | N/A | N/A | N/A | 3(95) | 13(71) | −2.5 |
| 17 | 3(95) | 6.5(41) | −13.8 | N/A | N/A | N/A | N/A | N/A | N/A | 2(100) | 5.9(54) | −12.1 |
| 18 | 1.3(97) | 8(40) | −9.3 | N/A | N/A | N/A | N/A | N/A | N/A | 4(100) | 6.3(37) | −26.1 |
| 19 | 4(94) | 5(47) | −51.5 | N/A | N/A | N/A | N/A | N/A | N/A | 5.1(100) | 9(47) | −13.4 |
| 20 | 14(98) | 69(40) | −1.1 | N/A | N/A | N/A | N/A | N/A | N/A | 14(100) | 16(40) | −32.8 |
| 21 | 17(98) | 20(45) | −19.3 | N/A | N/A | N/A | N/A | N/A | N/A | 8(98) | 19(42) | −4.9 |
| 22 | 4.4(98) | 5.8(41) | −42.8 | N/A | N/A | N/A | N/A | N/A | N/A | 1.8(100) | 6.8(37) | −12.7 |
| 23 | 1(98) | 4.5(35) | −14.2 | 1(100) | 4.3(60) | −16.4 | N/A | N/A | N/A | 1(94) | 6.5(35) | −9.1 |
| 24 | 5.3(95) | 6.4(20) | −63.7 | N/A | N/A | N/A | N/A | N/A | N/A | 1(91) | 5.4(31) | −12.5 |
| 25 | 1(98) | 5.5(42) | −14.4 | 2.2(100) | 5.3(55) | −14.5 | 2(100) | 3.5(13) | −45.9 | 2.3(100) | 6(28) | −20.4 |
| Slope (Median) | | | −15 | | | 0 | | | 0 | | | −20.4 |
| Range | | | (−63.9, −1.057) | | | (−40.67, 0) | | | (−45.89, 0) | | | (−65, −2.485) |

BIS vs. SEF95 vs. MEF vs. ApEn, p < 0.05 using Kruskal Wallis Test
BIS vs. SEF95, p < 0.05 using Mann-Whitney Rank Sum Test
BIS vs. MEF, p < 0.05 using Mann-Whitney Rank Sum Test
BIS vs. ApEn, p > 0.05 using Mann-Whitney Rank Sum Test Table 6 shows variation of sensitivities of these four analytical methods, i.e., BIS Index, SEF95, MEF and approximate entropy. Their median values of slopes were −15, 0, 0, and −20.4, respectively. Thus, after intravenous injecting the subject with thiopental, these medium values in top-down order were successively as approximate entropy, BIS Index, SEF95 and MEF.

Since values from these 4 types of analytical methods did not show normal distribution, a non-parametric statistical method of Kruskal Wallis Test was used to cross compare BIS Index, SEF95, MEF and approximate entropy with one another in order to reveal whether there were significant differences in the anesthesia course among them. The obtained p value was less than 0.05, indicating that there were differences among these 4 analytical methods. Furthermore, a difference analysis of Mann-Whitney Rank Sum Test was conducted over results from these 4 analytical methods. As the result, p value for the difference between SEF95 and BIS Index, and between MEF and BIS Index, were less than 0.05, indicating both SEF95 and MEF differed significantly from BIS Index. Further, slopes of SEF95 and MEF were less than that of BIS Index, indicating both of SEF95 and MEF exhibited sensitivities to the drug inferior to that of BIS Index.

In addition, no difference existed between approximate entropy and BIS (p>0.05), which represented, after intravenous injecting the subject with thiopental, both approximate entropy and BIS Index could display rapidly a sensitivity in response to the metabolism of the drug. Moreover, the slope value (−20.4) obtained from approximate entropy analysis was the greatest one among those obtained from four methods, which indicated that approximate entropy not only could differentiate the course from conscious to anesthesia, but also could respond rapidly to the change from conscious to anesthesia of the subject immediately after intravenous injection with thiopental.

Next, in the recovery phase of anesthesia, these 4 analytical methods, i.e., BIS Index, SEF95, MEF and approximate entropy, were compared with one another in terms of the sensitivity to the metabolism of the drug from anesthesia to conscious state of the subject.

As the subject entered the recovery phase of anesthesia, the slope of the line from the minimum value to the maximum value of the depth of anesthesia obtained from each analytical method was used to determine the sensitivity of the respective analytical theory to the metabolism of the drug. For this, the minimum value of depth of anesthesia from BIS Index was assumed to be $B_3$, while its maximum value was assumed to be $B_4$. The minimum value of depth of anesthesia from SEF95 was assumed to be $S_3$, while its maximum value was assumed to be $S_4$. The minimum value of depth of anesthesia from MEF was assumed to be $M_3$, while its maximum value was assumed to be $M_4$. The minimum value of depth of anesthesia from approximate entropy was assumed to be $A_3$, while its maximum value was assumed to be $A_4$. Values of $B_3$, $B_4$, $S_3$, $S_4$, $M_3$, $M_4$, $A_3$ and $A_4$ from each of the subject were shown in FIG. 3-1 to 3-25. Thereafter, the difference between the time at each point of the above-described $B_3$, $B_4$, $S_3$, $S_4$, $M_3$, $M_4$, $A_3$ and $A_4$ and the time the recovery phase of anesthesia started was defined as the relative time. The relative time of each analytical method was expressed as BIS($B_3'$, $B_4'$), SEF95($S_3'$, $S_4$), MEF($M_3'$, $M_4'$), and approximate entropy ($A_3'$, $A_4'$). Then, the sensitivity of each of these 4 analytical methods to the brain wave change was compared using the slope between two points. The result was shown in Table 7.

were no differences among these 4 analytical methods. Furthermore, a difference analysis of Mann-Whitney Rank Sum

TABLE 7

Comparison among sensitivities of BIS Index, SEF95, MEF and approximate entropy to the recovery phase of anesthesia

| | BIS | | | SEF95 | | | MEF | | | ApEn | | |
|---|---|---|---|---|---|---|---|---|---|---|---|---|
| Patient | $B_3'$ | $B_4'$ | slope | $S_3'$ | $S_4'$ | slope | $M_3'$ | $M_4'$ | slope | $A_3'$ | $A_4'$ | slope |
| 1 | 44(30) | 46.9(82) | 20.9 | N/A | N/A | N/A | N/A | N/A | N/A | 44.7(17) | 45.9(91) | 62 |
| 2 | 154.9(51) | 179.5(84) | 1.3 | N/A | N/A | N/A | N/A | N/A | N/A | 149.3(51) | 179.3(95) | 1.5 |
| 3 | 151(39) | 157(92) | 8.7 | N/A | N/A | N/A | N/A | N/A | N/A | 149.6(21) | 156.5(85) | 9.3 |
| 4 | 80(25) | 93(80) | 4.2 | 79.6(26) | 93(91) | 5 | 79.8(11) | 93(93) | 6.3 | 84(18) | 94(81) | 6.5 |
| 5 | 85(34) | 105(75) | 2 | 78.6(38) | 100(83) | 2.1 | 87(17) | 106(100) | 4.3 | 88.5(52) | 101.6(82) | 2.3 |
| 6 | 68(36) | 71(94) | 16.6 | 70.7(46) | 73(66) | 10.8 | 71(18) | 73(55) | 14.7 | 63(48) | 72(100) | 5.7 |
| 7 | 72(37) | 75(94) | 16 | 72(45) | 78(98) | 8.7 | 71(20) | 75(67) | 12.1 | 69(27) | 73(99) | 18 |
| 8 | 144(32) | 163(96) | 3.3 | 145(40) | 164(97) | 3.1 | 145(17) | 163(70) | 3 | 152(35) | 161(93) | 18 |
| 9 | 161(48) | 174(97) | 4 | 171(50) | 175(97) | 10.9 | 171(21) | 175(97) | 18 | 149(60) | 175(97) | 1.4 |
| 10 | 137(35) | 155(96) | 3.3 | 135(36) | 155(84) | 2.4 | 132(12) | 152(83) | 3.5 | 138(43) | 156(98) | 3.2 |
| 11 | 101(39) | 111(84) | 4.7 | 99(50) | 111(98) | 3.9 | 98(20) | 110(87) | 6 | 91(35) | 111(81) | 2.3 |
| 12 | 109(44) | 125(98) | 3.3 | 21(47) | 126(100) | 10.9 | 118(17) | 126(86) | 9 | 122(36) | 127(99) | 13 |
| 13 | 97(26) | 109(95) | 5.8 | 96(32) | 105(96) | 6.9 | 95(18) | 104(87) | 8 | 94(36) | 107(100) | 5.3 |
| 14 | 105(34) | 125(97) | 3.1 | 108(35) | 126(91) | 3.1 | 106(15) | 119(88) | 5.3 | 107(44) | 105(93) | 6 |
| 15 | 104(50) | 108(86) | 9.1 | 90(56) | 108(100) | 2.5 | 90(36) | 108(100) | 3.6 | 97(45) | 105(93) | 6 |
| 16 | 42(39) | 50(90) | 6.5 | 141(60) | 149(100) | 4.5 | 41(20) | 50( )80 | 6.7 | 39(40) | 47(100) | 8 |
| 17 | 138(35) | 148(98) | 5.9 | 133(47) | 148(100) | 3.4 | 139(24) | 147(67) | 5.4 | 128(38) | 147(96) | 3.1 |
| 18 | 150(21) | 169(81) | 3.3 | 141(35) | 168(100) | 2.4 | 154(12) | 168(100) | 6.2 | 138(30) | 169(85) | 1.8 |
| 19 | 145(33) | 169(87) | 2.2 | 145(39) | 171(83) | 1.7 | 144(9) | 168(51) | 2 | 145(27) | 170(85) | 2.3 |
| 20 | 73(33) | 84(95) | 5.6 | 73(44) | 84(80) | 3.2 | 73(15) | 84(60) | 4.1 | 73(61) | 87(100) | 2.3 |
| 21 | 72(40) | 87(95) | 3.8 | 72(44) | 85(100) | 4.3 | 72(14) | 85(100) | 6.3 | 74(56) | 85(93) | 3.5 |
| 22 | 44(34) | 61(94) | 3.6 | 44(47) | 61(100) | 3.2 | 44(14) | 58(83) | 4.8 | 43(47) | 58(100) | 3.7 |
| 23 | 60(41) | 77(81) | 2.4 | 60(47) | 74(73) | 1.8 | 60(19) | 77(59) | 2.4 | 61(47) | 76(99) | 3.4 |
| 24 | 91(28) | 104(98) | 5.4 | 89(40) | 105(97) | 3.6 | 96(16) | 102(82) | 12.2 | 97(36) | 100(100) | 21.3 |
| 25 | 71(43) | 87(73) | 1.8 | 60(55) | 87(90) | 1.3 | 52(22) | 93(89) | 1.6 | 28(68) | 93(99) | 2.5 |
| Slope (Median) | | 4 | | | 3.2 | | | 5.3 | | | 3.5 | |
| Range | | (1.3, 20.9) | | | (0, 10.9) | | | (0, 17.6) | | | (1.4, 62) | |

BIS vs. SEF95 vs. MEF vs. ApEn, p > 0.05 using Kruskal Wallis Test
BIS vs. SEF95, p > 0.05 using Mann-Whitney Rank Sum Test
BIS vs. MEF, p > 0.05 using Mann-Whitney Rank Sum Test
BIS vs. ApEn, p > 0.05 using Mann-Whitney Rank Sum Test Table 7 shows variation of sensitivities of these four analytical methods, i.e., BIS Index, SEF95, MEF and approximate entropy. Their median values of slopes were 4, 3.2, 5.3, and 3.5, respectively. These medium values in top-down order were successively as MEF, BIS Index, approximate entropy and SEF95. Since values from these 4 types of analytical methods did not show normal distribution, a non-parametric statistical method of Kruskal Wallis Test was used to cross compare BIS Index, SEF95, MEF and approximate entropy with one another in order to reveal whether there were significant differences in the anesthesia course among them. The obtained p value was higher than 0.05, indicating that there Test was conducted over results from these 4 analytical methods. As the result, all of the p values for the difference between SEF95 and BIS Index, between MEF and BIS Index, and between approximate entropy and BIS Index were higher than 0.05, indicating all of these four methods exhibited quite good sensitivity with respect to the metabolism of the anesthesia gas.

Finally, the anesthesia was divided into phases of induction, maintenance and recovery, and investigated the change of depth of anesthesia in 25 subjects using statistical method, as shown in Table 8.

TABLE 8

Statistical analysis of BIS Index, SEF95, MEF and approximate entropy in various anesthesia phases

| | Kruskal Wallis Test | | | Mann-Whitney Rank Sum Test | |
|---|---|---|---|---|---|
| | Number | Median (Range) | P < 0.05 | | P < 0.05 |
| BIS(Induction) | 25 | 80.6 (67.7, 89.2) | yes | BIS(Induction) vs. BIS(Maintenance) | yes |
| BIS(Maintenance) | 25 | 46.7 (29.5, 64.6) | | BIS(Induction) vs. BIS(Recovery) | yes |
| BIS(Recovery) | 25 | 61.4 (47.8, 72.8) | | BIS(Recovery) vs. BIS(Maintenance) | yes |
| SEF95(Induction) | 25 | 60.4 (45.2, 82.9) | Yes | SEF95(Induction) vs. SEF95(Maintenance) | no |
| SEF95(Maintenance) | 25 | 54.8 (40.5, 70.1) | | SEF95(Induction) vs. SEF95(Recovery) | yes |
| SEF95(Recovery) | 25 | 69.7 (53.6, 87.9) | | SEF95(Recovery) vs. SEF95(Maintenance) | yes |
| MEF(Induction) | 25 | 27.1 (17.1, 56.2) | yes | MEF(Induction) vs. MEF(Maintenance) | no |
| MEF(Maintenance) | 25 | 30.3 (15.9, 46.6) | | MEF(Induction) vs. MEF(Recovery) | yes |
| MEF(Recovery) | 25 | 47.3 (26.1, 67.2) | | MEF(Recovery) vs. MEF(Maintenance) | yes |
| ApEn(Induction) | 25 | 77.2 (61.8, 88.8) | yes | ApEn(Induction) vs. ApEn(Maintenance) | yes |

TABLE 8-continued

Statistical analysis of BIS Index, SEF95, MEF and approximate entropy in various anesthesia phases

| | Kruskal Wallis Test | | | Mann-Whitney Rank Sum Test | |
|---|---|---|---|---|---|
| | Number | Median (Range) | $P < 0.05$ | | $P < 0.05$ |
| ApEn(Maintenance) | 25 | 52.8 (18.8, 69.7) | | ApEn(Induction) vs. ApEn(Recovery) | no |
| ApEn(Recovery) | 25 | 72.6 (56.2, 84.9) | | ApEn(Recovery) vs. ApEn(Maintenance) | Yes |

As shown in Table 8, a Kruskal Wallis Test was conducted to analyze results from BIS Index, SEF95, MEF and approximate entropy to reveal whether there was any difference. As a result, p values from these four methods were all less than 0.05, indicating that there were significant differences among these four analytical methods in the three phases of anesthesia.

Furthermore, a Mann-Whitney Rank Sum Test was conducted to analyze various methods in order to reveal whither there were any difference among analytical results in the induction, maintenance and recovery phases obtained from various methods. Where, $p>0.05$ indicated no difference with one another. On the contrary, $p<0.05$ indicated a significant difference with one another. As shown in Table 8, no difference ($p>0.05$) existed between SEF95 and MEF with respect the result obtained in the induction and maintenance phases, which indicated that both of SEF95 and MEF failed to differentiate the conscious states of the subject in the induction and maintenance phases.

On the other hand, there were significant difference ($p<0.05$) between analytical results in the induction and maintenance phases, as well as between analytical results in the recovery and maintenance phases obtained from BIS Index and approximate entropy, which represented that both of BIS Index and approximate entropy were able to differentiate effectively the conscious state and anesthesia state of a subject. It is worthy to note that there was no difference ($p=0.05$) between approximate entropy analytical results in the induction phase and in the recovery phase, which indicated that approximate entropy could present the course of regaining a conscious state before anesthesia from the end of anesthesia for a subject.

It can be seen from the above-described analytical results that conscious states of a subject in various anesthesia phases not only can be differentiated by approximate entropy, but also the analytical result of approximate entropy is the best one among the four methods, i.e., BIS Index, SEF95, MEF and approximate entropy.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

REFERENCES

1. Schwilden H., Stoeckel H., "Quantitative EEG analysis during anaesthesia with isoflurane in nitrous oxide at 1.3 and 1.5 MAC". Br. J. Anaesth., vol. 59, pp. 738-45, 1987.
2. Katoh T., Suzuki A., Ikeda K., "Electroencephalographic derivatives as a tool for predicting the depth of sedation and anesthesia induced by sevoflurane", Anesthesiology, vol. 88, pp. 642-50, 1998.
3. Miyashita T., Ogawa K., Itoh H., Arai Y., Ashidagawa M., Uchiyama M., Koide Y., Andoh T., Yamada Y., "Spectral analyses of electroencephalography and heart rate variability during sleep in normal subjects". Autonomic Neuroscience: Basic and Clinical, vol. 103, pp. 114-120, 2003.
4. Billard V., Gambus P. L., Chamoun N., Stanski D. R., Shafer S. L., "A comparison of spectral edge, delta power, and bispectral index as EEG measures of alfentanil, propofol, and midazolam drug effect." Clin. Pharmacol. Ther., vol. 61, pp. 45-58, 1997.
5. Elbert T., Ray W. J., Kowalik Z. J., Skinner J. E., Graf K. E., Birbauer N., "Chaos and physiology: Deterministic chaos in excitable cell assemblies", Physiol. Rev., vol. 74, pp. 1-47, 1994.
6. Pritchard W. S., Duke D. W., "Measuring chaos in the brain: A tutorial review of nonlinear dynamical analysis." Brain J. Neurosci. vol. 67, pp. 31-80, 1992.
7. Fell J., Roschke J., Mann K., Schaffner C., "Discrimination of sleep stages: A comparison between spectral and nonlinear EEG measures.", Electroencephalogr Clin. Neurophysiol., vol. 98, pp. 401-10, 1996.
8. Grassberger P., Procaccia I., "Estimation of the Kolmogorov entropy from a chaotic signal." Phys. Rev., vol. A28, pp. 2591-3, 1983.
9. Eckmann J. P., Ruelle D., "Ergodic theory of chaos and strangeattractors." Rev. Mod. Phys., vol. 57, pp. 617-56, 1985.
10. Bruhn J., Ropcke H., Hoeft A., "Approximate Entropy as an Electroencephalographic Measure of Anesthetic Drug Effect during Desflurane Anesthesia", Anesthesiology, vol. 92, pp. 715-26, 2000.
11. Yeragania V. K., Pohla R., Mallavarapub M., Balona R., "Approximate entropy of symptoms of mood: an effective technique to quantify regularity of mood", Bipolar Disorders, vol. 5, pp. 279-286, 2003.
12. Diambra L., Bastos de Figueiredo J. C., Malta C. P., "Epileptic activity recognition in EEG recording", Elsevier Physica. A., vol. 273, pp. 495-505, 1999.
13. Schuckers S. A., "Use of Approximate Entropy Measurements to Classify Ventricular Tachycardia and Fibrillation", J. Electrocardiology, vol. 31, pp. 101-105, 1998.

What is claimed is:

1. A method for predicting the depth of anesthesia, comprising steps of:

attaching measuring patch on the center, ground, and right of the brow of a human subject and using an electroencephalography monitor to measure electroencephalogram from the human subject being tested;

recording the electroencephalography data from the electroencephalography monitor in the induction phase of anesthesia course;

calculating an approximate entropy value from the recorded electroencephalogram signal by using the formula:

Approximate Entropy=$\Phi^m(r)-\Phi^{m+1}(r)$;

$$\Phi^m(r) = (N-m+1)^{-1} \cdot \sum_{i=1}^{N-m+1} \ln C_i^m(r);$$

wherein
$C_i^m(r)$=(number of x(j) such that d[x(i),x(j)]≦r)/(N−m+1);
x(i)=[u(i), . . . , u(i=m−1)];
x(j)=[u(j), . . . , u(j=m−1)];
u(i),u(2) . . . u(N) are time sequence data;
u(i),u(2) . . . u(N) are time sequence data;
wherein N is the length of data cycle;
m is the number of data comparison;
r is a noise filtering coefficient;
computing a corrected approximate entropy value by multiplying the approximate entropy value and 1000/17;
displaying the corrected approximate entropy value on a monitor as the subject's the depth of anesthesia state, wherein the displayed entropy value of 70-100 indicates that the subject is in a conscious state or slightly tranquilized state; the displayed entropy value of 60-70 indicates that the subject is in a slight non-conscious state; the displayed entropy value of 40-60 indicates that the subject is in a non-conscious state; and the displayed entropy value of 0-40 indicates that the subject is in an excessively non-conscious state.

2. A method for predicting the depth of anesthesia as recited in claim 1, wherein the sampling time of the original electroencephalogram is 1/256 to 1/128 second/time.

3. A method for predicting the depth of anesthesia as recited in claim 1, wherein the computer recorded 1024 electroencephalography data point each time for computation.

4. A method for predicting the depth of anesthesia as recited in claim 1, wherein the predicting value of depth of anesthesia represents the degree of consciousness state or the depth of anesthesia of one being tested.

5. A method for predicting the depth of anesthesia, comprising steps of:
attaching measuring patch on the center, ground, and right of the brow of a human subject and using an electroencephalography monitor to measure electroencephalogram from the human subject being tested;
recording the electroencephalography data from the electroencephalography monitor in the recovery phase of anesthesia course;
calculating an approximate entropy value from the recorded electroencephalogram signal by using the formula:

Approximate Entropy=$\Phi^m(r)-\Phi^{m+1}(r)$;
wherein $$\Phi^m(r) = (N-m+1)^{-1} \cdot \sum_{i=1}^{N-m+1} \ln C_i^m(r);$$

$C_i^m(r)$=(number of x(j) such that d[x(i),x(j)]≦r)/(N−m+1);
x(i)=[u(i), . . . , u(i=m−1)];
x(j)=[u(j), . . . , u(j=m−1)];
u(i),u(2) . . . u(N) are time sequence data;
u(i),u(2) . . . u(N) are time sequence data;
wherein N is the length of data cycle;
m is the number of data comparison;
r is a noise filtering coefficient;
computing a corrected approximate entropy value by multiplying the approximate entropy value and 1000/17;
displaying the corrected approximate entropy value on a monitor as the subject's the depth of anesthesia state, wherein the displayed entropy value of 70-100 indicates that the subject is in a conscious state or slightly tranquilized state; the displayed entropy value of 60-70 indicates that the subject is gradually restoring the conscious state; the displayed entropy value of 40-60 indicates that the subject is in a non-conscious state; and the displayed entropy value of 0-40 indicates that the subject is in an excessively non-conscious state.

6. A method for predicting the depth of anesthesia as recited in claim 5, wherein the sampling time of the original electroencephalogram is 1/256 to 1/128 second/time.

7. A method for predicting the depth of anesthesia as recited in claim 5, wherein the computer recorded 1024 electroencephalography data point each time for computation.

8. A method for predicting the depth of anesthesia as recited in claim 5, wherein the predicting value of depth of anesthesia represents the degree of consciousness state or the depth of anesthesia of one being tested.

* * * * *